US010213263B2

(12) United States Patent
Hyodo et al.

(10) Patent No.: US 10,213,263 B2
(45) Date of Patent: Feb. 26, 2019

(54) FLEXIBLE-MANIPULATOR GUIDE MEMBER AND FLEXIBLE MANIPULATOR

(71) Applicant: OLYMPUS CORPORATION, Tokyo (JP)

(72) Inventors: Ryoji Hyodo, Tokyo (JP); Kosuke Kishi, Tokyo (JP); Noriaki Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 238 days.

(21) Appl. No.: 15/180,139

(22) Filed: Jun. 13, 2016

(65) Prior Publication Data

US 2016/0287346 A1 Oct. 6, 2016

Related U.S. Application Data

(63) Continuation of application No. PCT/JP2014/083744, filed on Dec. 19, 2014.

(60) Provisional application No. 61/918,808, filed on Dec. 20, 2013.

(51) Int. Cl.
*A61B 34/00* (2016.01)
*A61B 34/30* (2016.01)

(52) U.S. Cl.
CPC .............. *A61B 34/71* (2016.02); *A61B 34/30* (2016.02); *A61B 2034/301* (2016.02)

(58) Field of Classification Search
CPC .............. A61B 34/71; A61B 2034/301; A61B 2034/302; A61B 2034/303; A61B 1/00071; A61B 1/005; A61B 1/0051; A61B 1/0052; A61B 1/0055; A61B 1/0057; A61B 18/1442; A61B 18/1445; A61B 17/29; A61B 17/2901; A61B 17/2905;
(Continued)

(56) References Cited

U.S. PATENT DOCUMENTS

| 4,745,908 A | 5/1988 | Wardle |
| 4,795,439 A | 1/1989 | Guest |
| 5,368,564 A | 11/1994 | Savage |

(Continued)

FOREIGN PATENT DOCUMENTS

| JP | H07-095994 B2 | 10/1995 |
| JP | 2137683 C3 | 7/1998 |

(Continued)

OTHER PUBLICATIONS

Extended Supplementary European Search Report dated Jul. 28, 2017 in European Patent Application No. 14 87 1900.8.
(Continued)

*Primary Examiner* — Robert Lynch
(74) *Attorney, Agent, or Firm* — Scully, Scott, Murphy & Presser, P.C.

(57) ABSTRACT

A flexible-manipulator guide member is provided in an inserted portion of a flexible manipulator including the elongated flexible inserted portion, the movable portion disposed at the distal end of the inserted portion, a drive portion disposed at the base end of the inserted portion, and the elongated driving-force transmitting member that transmits motive power of the drive portion to the movable portion, and is provided with a lumen through which the driving-force transmitting member passes in the longitudinal direction, wherein the lumen has a twisted shape about the longitudinal axis of the inserted portion.

10 Claims, 22 Drawing Sheets

(58) Field of Classification Search
CPC ...... A61M 2025/004; A61M 2025/015; A61M 25/0012; A61M 25/0141; A61M 25/0147
See application file for complete search history.

(56) References Cited

U.S. PATENT DOCUMENTS

| | | |
|---|---|---|
| 5,507,725 A | 4/1996 | Savage et al. |
| 5,571,085 A | 11/1996 | Accisano, III |
| 7,135,008 B2 | 11/2006 | O'Mahony et al. |
| 7,662,091 B2 | 2/2010 | Bagley et al. |
| 7,744,608 B2 | 6/2010 | Lee et al. |
| 2005/0277862 A1 | 12/2005 | Anand |
| 2007/0112355 A1 | 5/2007 | Salahieh et al. |
| 2008/0132834 A1 | 6/2008 | Melville |
| 2011/0009863 A1 | 1/2011 | Marczyk et al. |
| 2011/0196419 A1 | 8/2011 | Cooper |
| 2012/0209315 A1 | 8/2012 | Amat Girbau |

FOREIGN PATENT DOCUMENTS

| | | |
|---|---|---|
| JP | 2000-185013 A | 7/2000 |
| JP | 2000-325298 A | 11/2000 |
| JP | 2003-523806 A | 8/2003 |
| JP | 2004-329933 A | 11/2004 |
| JP | 3628385 B2 | 3/2005 |
| JP | 2008-504897 A | 2/2008 |
| JP | 2008-509785 A | 4/2008 |
| JP | 2008-237810 A | 10/2008 |
| JP | 2009-066299 A | 4/2009 |
| JP | 4349685 B2 | 10/2009 |
| JP | 4420593 B2 | 2/2010 |
| JP | 2010-511440 A | 4/2010 |
| JP | 2010-137067 A | 6/2010 |
| JP | 2010-227137 A | 10/2010 |
| JP | 2013-508107 A | 3/2013 |
| JP | 2013-518665 A | 5/2013 |
| JP | 2013-111110 A | 6/2013 |
| JP | 2013-172780 A | 9/2013 |
| JP | 2013-172781 A | 9/2013 |
| WO | 94/14494 A2 | 7/1994 |
| WO | WO 01/058397 A1 | 8/2001 |
| WO | WO 2006/014339 A2 | 2/2006 |
| WO | WO 2006/023343 A2 | 3/2006 |
| WO | WO 2008/070556 A | 6/2008 |
| WO | 2011/005335 A1 | 1/2011 |
| WO | WO 2011/051253 A1 | 5/2011 |
| WO | WO 2011/097095 A1 | 8/2011 |

OTHER PUBLICATIONS

International Search Report dated Mar. 24, 2015 issued in PCT/JP2014/083744.

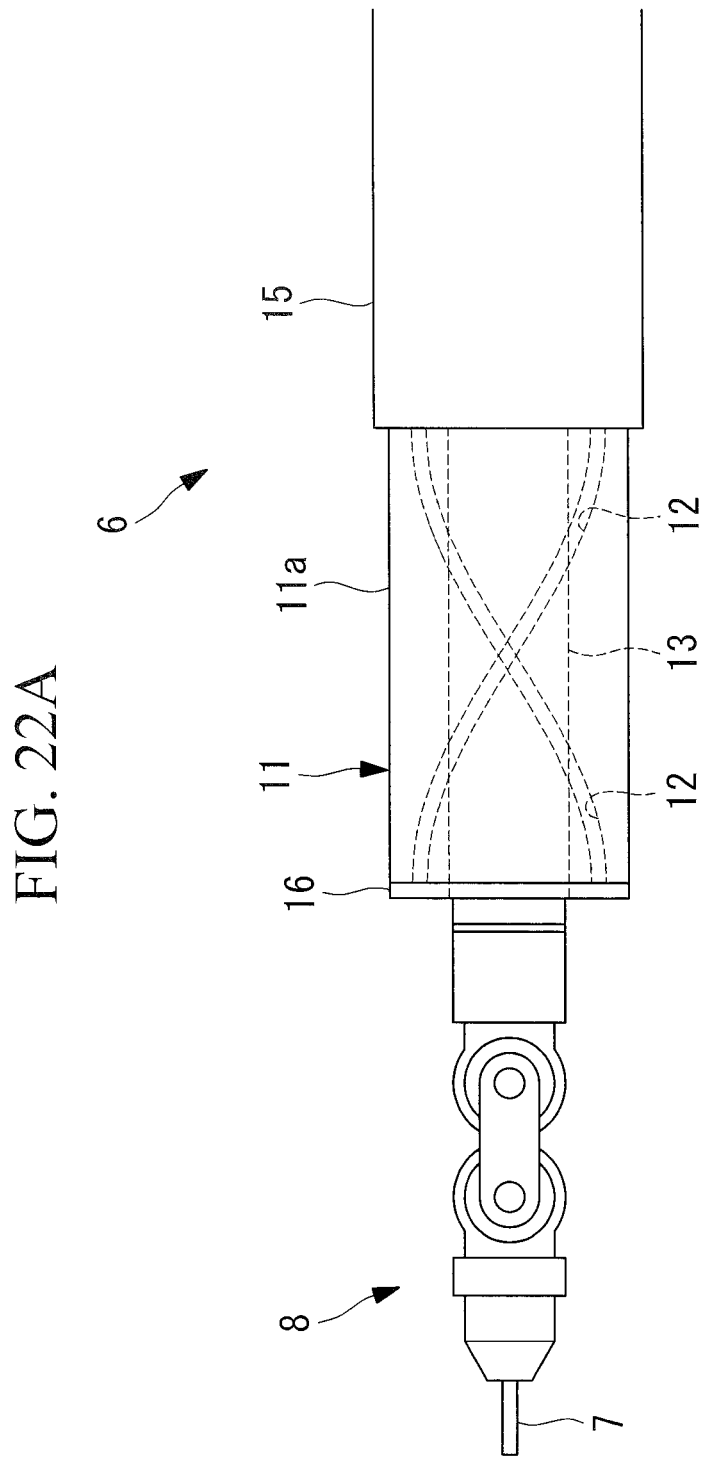

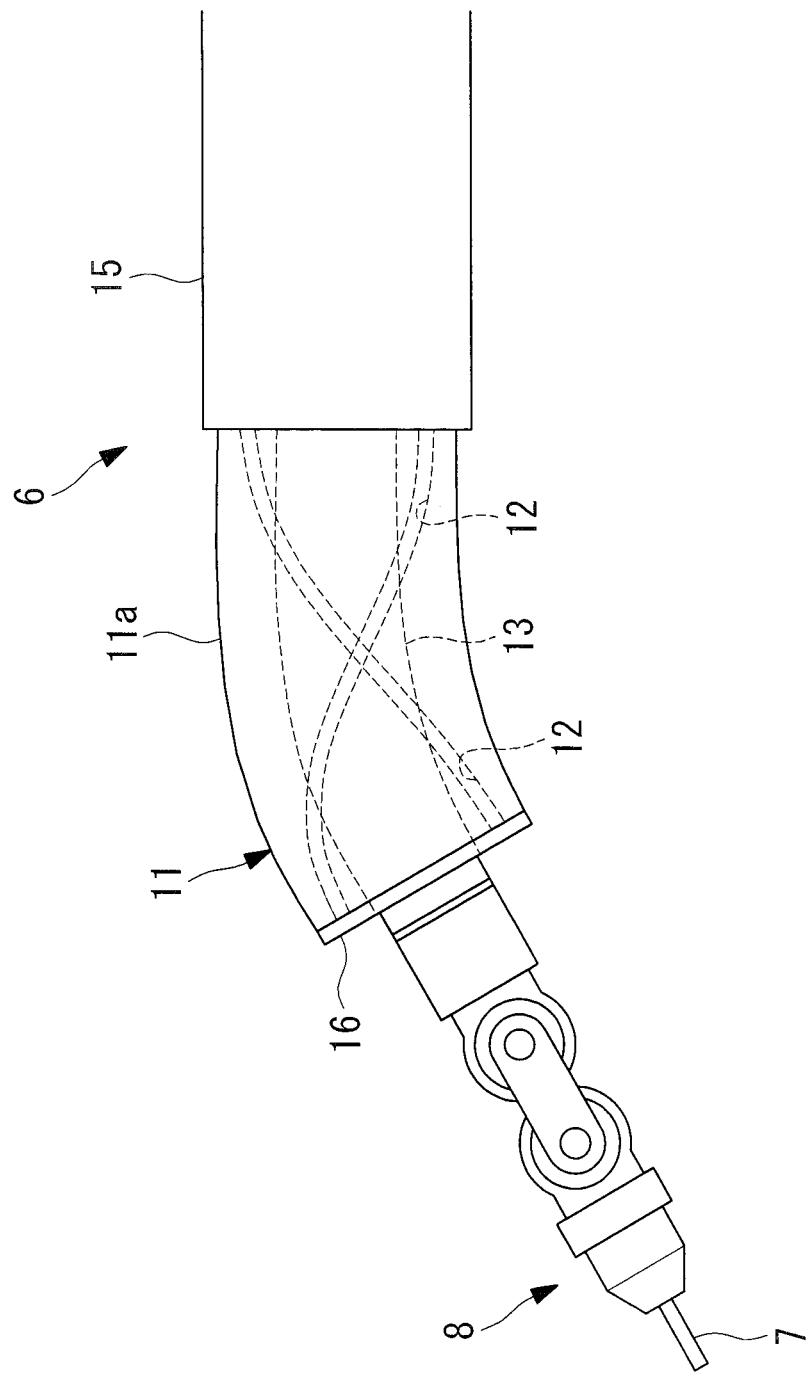

FLEXIBLE-MANIPULATOR GUIDE MEMBER AND FLEXIBLE MANIPULATOR

CROSS-REFERENCE TO RELATED APPLICATIONS

This is a continuation of International Application PCT/JP2014/083744, with an international filing date of Dec. 19, 2014, which is hereby incorporated by reference herein in its entirety. This application claims the benefit of U.S. Provisional Patent Application No. 61/918,808, filed on Dec. 20, 2013, the content of which is incorporated herein by reference.

TECHNICAL FIELD

The present invention relates to a flexible-manipulator guide member and a flexible manipulator.

BACKGROUND ART

There are known endoscopes, catheters, or manipulators employing a system in which a bending portion or a movable portion such as forceps or the like that is disposed at a distal end of an inserted portion is driven by using a wire (for example, see Patent Literatures 1 to 8).

Patent Literature 1 discloses a flexible manipulator in which the diameter is reduced and a cost reduction is achieved by eliminating an insulation film and a coil sheath by guiding wires, which are used to drive a movable portion, such as forceps or the like disposed at a distal end of a flexible inserted portion, so as to pass through a lumen formed straight along the longitudinal direction of a multi-lumen tube disposed in the inserted portion.

In addition, Patent Literature 2 discloses a rigid manipulator in which a plurality of wires that pass through a joint, which is disposed at a distal end of a rigid inserted portion, and that are used to drive a movable portion, such as forceps or the like, disposed farther on the distal-end side than the joint is, are individually made to pass through a plurality of sheaths, which pass through the inserted portion and the joint, and the sheaths are twisted at the position of the joint, thus compensating for the differences in the path lengths caused by flexing of the joint.

In addition, in order to prevent the flexural rigidity of a multi-lumen tube having partitions that radially section the interior of the tube from becoming non-uniform depending on the positions of the partitions, Patent Literature 3 discloses a medical tube in which the partitions are twisted along the longitudinal direction.

In addition, in order to enhance the flexing performance of a flexing portion disposed at a distal end of a flexible inserted portion, Patent Literature 4 discloses a catheter tube having multiple lumens in which the lumens through which a wire to passes through are twisted by 90° in the inserted portion and the flexing portion.

In addition, in order to prevent a wire guide disposed inside a flexible pipe from pressing or damaging other built-in objects inside the flexible pipe, Patent Literature 5 discloses an endoscope inserted portion in which a wire guide formed of a coil pipe that is twisted, inside the flexible pipe, about the axis of the flexible pipe is secured to an inner surface of the flexible pipe.

In addition, Patent Literature 6 discloses an endoscope in which a bending-manipulation wire passes through straight along the longitudinal direction inside a lumen disposed at the center in a radial direction, and, inside a lumen disposed in the surrounding area thereof in a spiraling manner, a signal line or the like passes through.

In addition, Patent Literature 7 discloses an endoscope in which bending-manipulation wires pass through lumens that are provided side-by-side along the longitudinal direction of a multi-lumen tube.

Furthermore, Patent Literature 8 discloses a catheter in which a lumen through which a bending-manipulation wire passes is disposed along the longitudinal axis of the catheter in a spiraling manner.

With the flexible manipulator of Patent Literature 1, because the lumens that guide the wires is formed straight along the longitudinal direction of the inserted portion, depending on the bending direction of the inserted portion, the path lengths of the two wires for manipulating the movable portion become different, and the movable portion is moved in an unintended direction when one wire tenses while making the other relaxed.

Patent Literature 2 relates to a joint portion of a rigid manipulator, and wire paths are assumed only for a bending portion that is actively bent in a set bending direction.

The object of Patent Literature 3 is to enhance the flexibility of a medical tube, and there is no description of wires for driving a movable portion.

Patent Literature 4 relates to wire paths for facilitating bending in a direction with a low flexural rigidity, and the wire paths are assumed only for a bending portion that is actively bent in a set bending direction.

Patent Literature 5 provides merely description of securing a wire guide formed of a coil pipe so as not to damage other built-in objects.

In Patent Literatures 6 and 7, because the path of the wire for driving the movable portion is formed straight along the longitudinal direction of the inserted portion, between the case in which the inserted portion is straight and the case in which the inserted portion is bent, there is a large change in frictional forces generated between the wire and the lumen, thus making the controllability poor.

Patent Literature 8 provides merely description of flexing and turning a distal end by compressing the catheter in accordance with the tensile forces in the wires.

CITATION LIST

Patent Literature

{PTL 1} Publication of Japanese Patent No. 4420593
{PTL 2} Japanese Translation of PCT International Application, Publication No. 2013-518665
{PTL 3} Publication of Japanese Patent No. 2137683
{PTL 4} Publication of Japanese Patent No. 3628385
{PTL 5} Publication of Japanese Patent No. 4349685
{PTL 6} Japanese Unexamined Patent Application, Publication No. 2000-185013
{PTL 7} Japanese Unexamined Patent Application, Publication No. 2009-66299
{PTL 8} Japanese Unexamined Patent Application, Publication No. 2010-227137

SUMMARY OF INVENTION

An aspect of the present invention is a flexible-manipulator guide member that is provided in an inserted portion of a flexible manipulator equipped with the elongated flexible inserted portion; a movable portion disposed at a distal end of the inserted portion; a drive portion disposed at a base end of the inserted portion; and an elongated driving-force transmitting member that transmits motive power of the drive portion to the movable portion, the flexible-manipulator guide member including a lumen through which the driving-force transmitting member passes in a longitudinal direction thereof, wherein the lumen has a twisted shape about a longitudinal axis of the inserted portion.

Another aspect of the present invention is a flexible-manipulator guide member that is provided in an inserted portion of a flexible manipulator equipped with the elongated flexible inserted portion; a movable portion disposed at a distal end of the inserted portion; a drive portion disposed at a base end of the inserted portion; and elongated driving-force transmitting members that transmit motive power of the drive portion to the movable portion, the flexible-manipulator guide member including three or more lumens through which the driving-force transmitting members pass in longitudinal directions thereof, wherein the lumens have a braided shape along the longitudinal axis of the inserted portion.

Another aspect of the present invention is a flexible manipulator including an elongated flexible inserted portion; a movable portion disposed at a distal end of the inserted portion; a drive portion disposed at a base end of the inserted portion; an elongated driving-force transmitting member that transmits motive power of the drive portion to the movable portion; and the above-described flexible-manipulator guide member.

Another aspect of the present invention is a flexible manipulator including an elongated flexible inserted portion; a movable portion disposed at a distal end of the inserted portion; a drive portion disposed at a base end of the inserted portion; an elongated driving-force transmitting member that transmits motive power of the drive portion to the movable portion; and the above-described flexible-manipulator guide member, wherein the flexible-manipulator guide member is provided with, separately from the lumen, a through-path that passes therethrough in the longitudinal direction.

BRIEF DESCRIPTION OF DRAWINGS

FIG. 22A is a side view showing an example of a multi-lumen tube in which a treatment tool passes through a center lumen thereof and that is bent by means of wires.

FIG. 22B is a side view showing the multi-lumen tube that has been bent from the state in FIG. 22A.

DESCRIPTION OF EMBODIMENT

A flexible-manipulator guide member 11 and a flexible manipulator 3 according to an embodiment of the present invention will be described with reference to the drawings.

Figure 1:
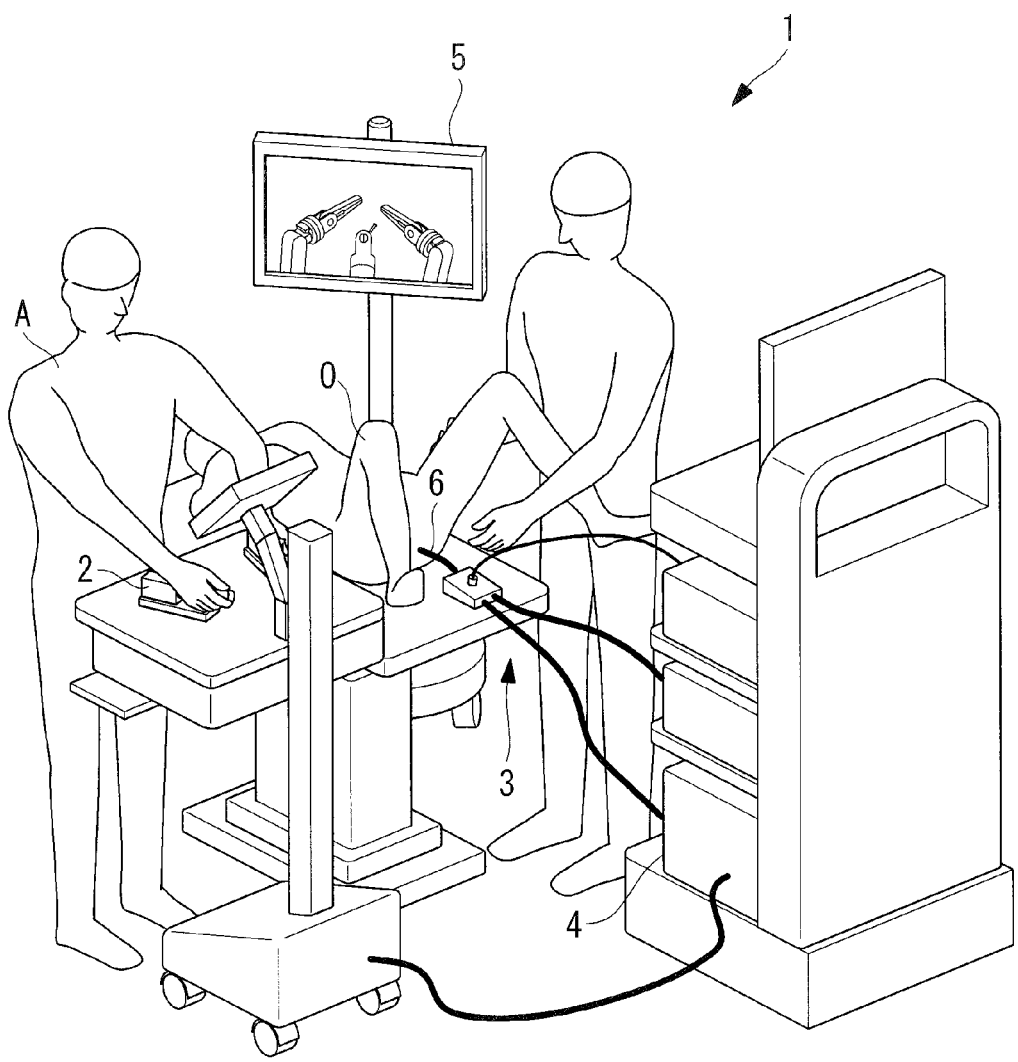
FIG. 1 is an overall configuration diagram showing a medical manipulator system provided with a flexible manipulator according to an embodiment of the present invention.

The flexible manipulator 3 according to this embodiment is employed in, for example, a medical manipulator system 1 shown in FIG. 1. This medical manipulator system 1 is provided with a master apparatus 2 that is manipulated by an operator A, a flexible manipulator 3 that is inserted into a body cavity of a patient O, a control portion 4 that controls the flexible manipulator 3 based on manipulation inputs to the master apparatus 2, and a monitor 5.

Figure 2:
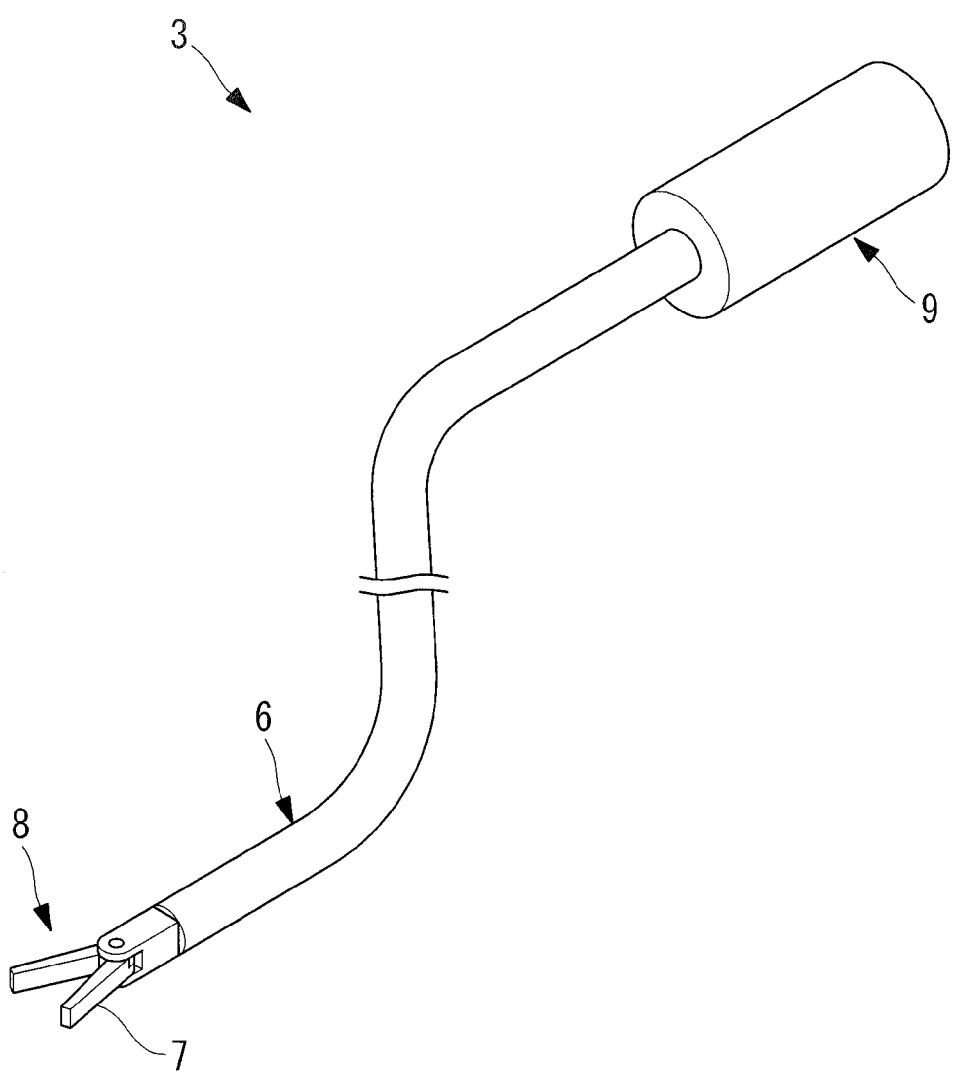
FIG. 2 is a perspective view showing an example of the flexible manipulator of FIG. 1.

As shown in FIG. 2, the flexible manipulator 3 according to this embodiment is provided with an inserted portion 6 that is inserted into the body cavity of the patient O, for example, via a forceps channel of an endoscope that is inserted into the body cavity of the patient O, a movable portion 8 that has a joint and a treatment portion 7 such as grasping forceps or the like that are disposed at the distal end of the inserted portion 6, a drive portion 9 that is disposed at the base end of the inserted portion 6 and that actuates the movable portion 8 by being controlled by the control portion 4, and wires (driving-force transmitting members, see FIG. 3) 10 that transmit a driving force generated by the drive portion 9 to the movable portion 8.

Figure 3:
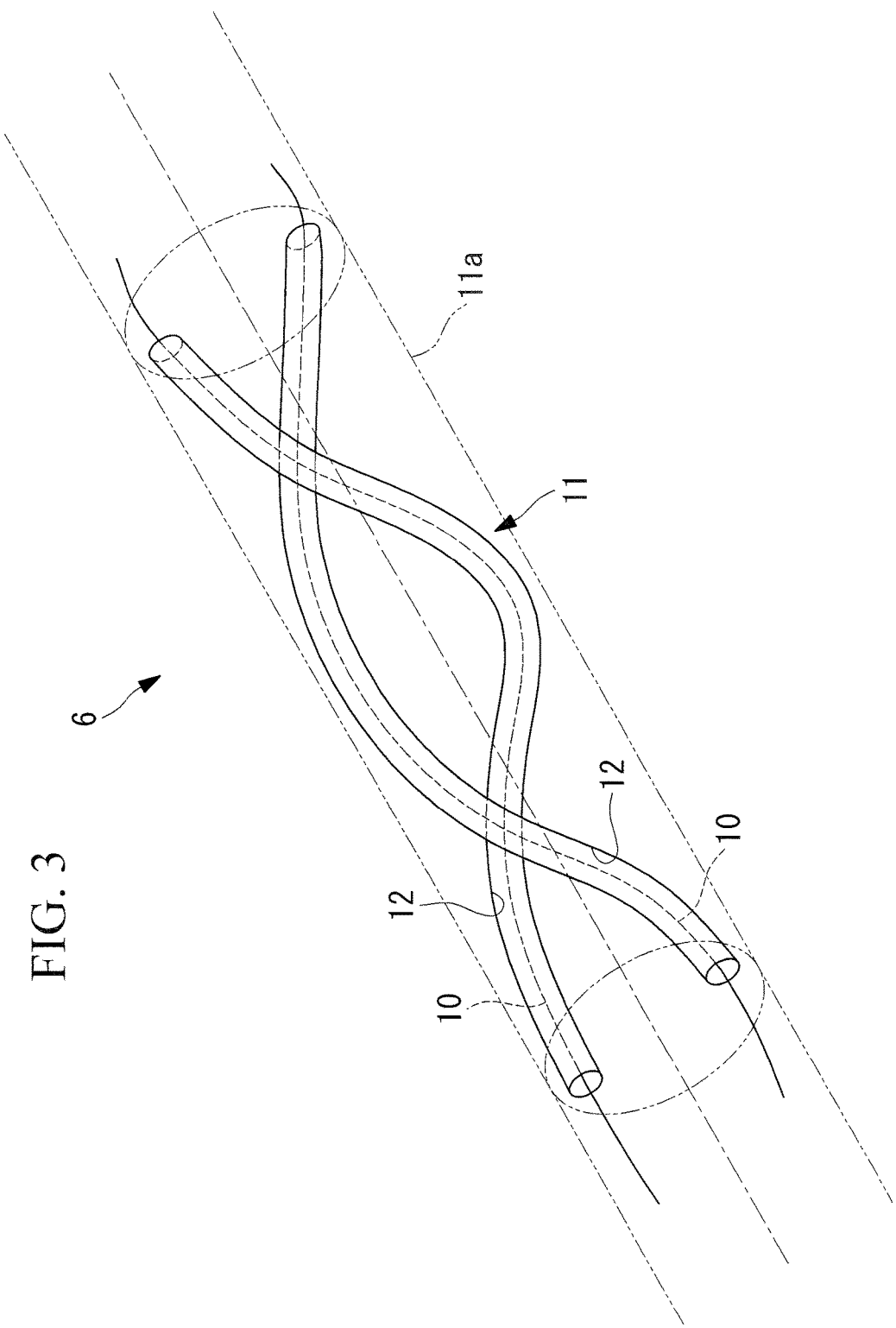
FIG. 3 is a perspective view partially showing lumens of a multi-lumen tube provided in an inserted portion of the flexible manipulator in FIG. 2.

The flexible-manipulator guide member 11 according to this embodiment is provided in the inserted portion 6. Specifically, as shown in FIG. 3, the flexible-manipulator guide member 11 is formed of a flexible material and is constituted of a multi-lumen tube 11a provided with a plurality of lumens 12 that pass therethrough in the longitudinal direction, and the configuration thereof is such that the wires 10 pass through the individual lumens 12. FIG. 3 partially shows a portion in the length direction of the flexible-manipulator guide member 11 formed of the multi-lumen tube 11a, and the flexible-manipulator guide member 11 is provided with two lumens 12 in the example shown in FIG. 3.

In this embodiment, the individual lumens 12 are formed in a spiral shape twisted in one direction about the longitudinal axis of the multi-lumen tube 11a at a constant pitch and a constant radius. It is desirable that the pitch be equal to or less than $2\pi r$, assuming that r is the minimum radius of curvature of the inserted portion 6.

The operation of the thus-configured flexible manipulator 3 and flexible-manipulator guide member 11 according to this embodiment will be described below.

In order to perform treatment inside the body cavity of the patient O by using the flexible manipulator 3 according to this embodiment, the operator A inserts the inserted portion 6 of the flexible manipulator 3 from the movable portion 8 side at the distal end via the forceps channel of the endoscope inserted into the body cavity of the patient O, and he/she makes the movable portion 8 face an affected site while observing an image acquired by the endoscope on the monitor 5.

Next, the operator A manipulates the master apparatus 2, thus inputting the amount by which the master apparatus 2 is manipulated to the control portion 4, and the control portion 4 generates driving forces in the drive portion 9 in accordance with the amount of manipulation, thus increasing the tensile force in one of the wires 10 more than the tensile force in the other wire 10. The driving forces applied to the wires 10 are transmitted to the movable portion 8 in the form of the tensile forces in the wires 10, and thus, the movable portion 8 is actuated. At this time, the wires 10 take spiral forms along the spiral lumens 12 by passing through the lumens 12 of the flexible-manipulator guide member 11.

Thus, the movement of the wires 10 caused by exertion of the tensile forces on the wires 10 is realized against frictional forces that are generated between the wires 10 and inner walls of the lumens 12. Specifically, the control portion 4 is configured so as to instruct the drive portion 9 so as to generate the driving forces in consideration of the frictional forces due to contact between the lumens 12 and the wires 10.

In this case, because the forceps channel provided in the inserted portion of the endoscope is bent in accordance with the shape of the body cavity into which the inserted portion is inserted, the inserted portion 6 of the flexible manipulator 3 inserted into the forceps channel is also bent in the same shape as that of the forceps channel.

Although the forms in which the inserted portion 6 is bent differ depending on individual variability and the degree of insertion into the body cavity, with the flexible-manipulator guide member 11 according to this embodiment, because the wires 10 are guided by the spiral lumens 12, the areas in which the wires 10 and inner surfaces of the lumens 12 come into contact do not greatly change regardless of whether the inserted portion 6 is stretched out straight or the inserted portion 6 is bent in a complex manner.

Therefore, with the flexible-manipulator guide member 11 and the flexible manipulator 3 according to this embodiment, the friction between the wires 10 and the inner surfaces of the lumens 12 do not greatly change depending on the forms in which the inserted portion 6 is bent, and thus, there is an advantage in that it is possible to facilitate the control of the drive portion 9 by the control portion 4.

Note that, although an example formed of the flexible multi-lumen tube 11a having numerous lumens 12 has been described as the flexible-manipulator guide member 11 according to this embodiment, alternatively, one or more flexible sheaths having one lumen 12 may be disposed inside the inserted portion 6 in a spiral form.

Figure 4A:
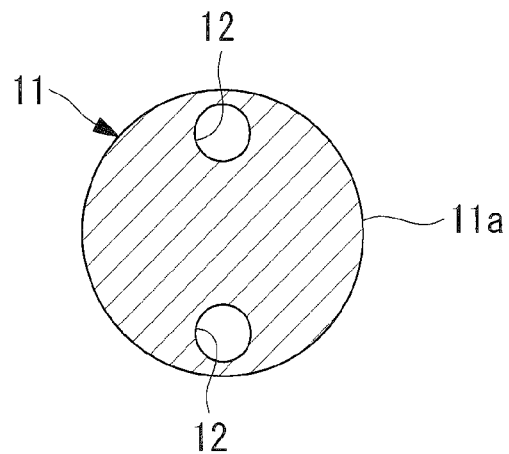
FIG. 4A is a lateral sectional view of the multi-lumen tube in FIG. 3.
Figure 4B:
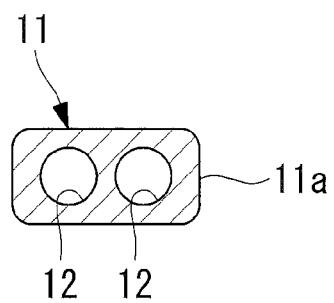
FIG. 4B is a lateral sectional view showing a first modification of the multi-lumen tube in FIG. 4A.

In addition, with regard to the transverse cross-sectional shape of the multi-lumen tube 11a, in addition to the circular shapes shown in FIGS. 3 and 4A, any arbitrary shapes may be employed, such as the rectangular shape shown in FIG. 4B or the like.

Figure 4C:
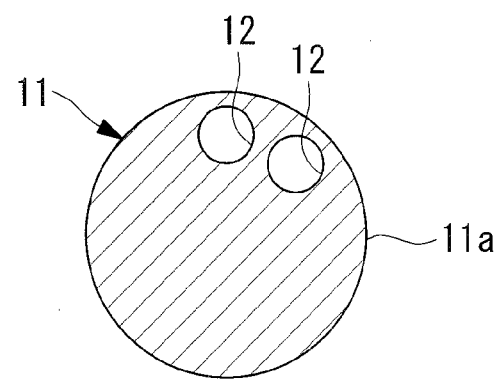
FIG. 4C is a lateral sectional view showing a second modification of the multi-lumen tube in FIG. 4A.
Figure 4D:
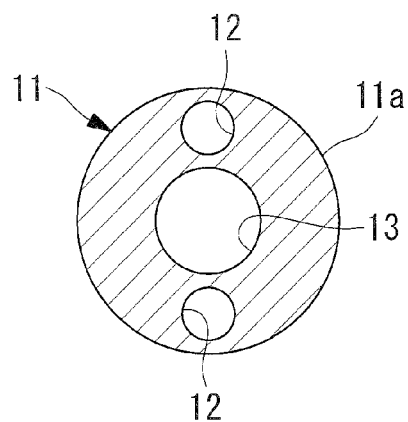
FIG. 4D is a lateral sectional view showing a third modification of the multi-lumen tube in FIG. 4A.
Figure 4E:
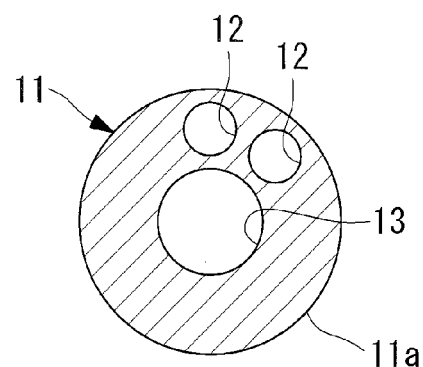
FIG. 4E is a lateral sectional view showing a fourth modification of the multi-lumen tube in FIG. 4A.

In addition, with regard to the positions of the lumens 12 in the multi-lumen tube 11a, the lumens 12 may be disposed at positions symmetrical with respect to the center of the transverse cross-section, as shown in FIG. 4A, or the lumens 12 may be disposed at adjacent positions in the circumferential direction, as shown in FIG. 4C. In addition, as shown in FIGS. 4D and 4E, a lumen (through-path) 13 that is used for other purposes or the like may be provided at the center.

In this case, because the center lumen 13 is disposed along the longitudinal axis of the multi-lumen tube 11a without being twisted like the other lumens 12, it is effective for allowing an elongated member for which twisting is not desirable, for example, an optical fiber or the like, to pass through the interior thereof.

Figure 5A:
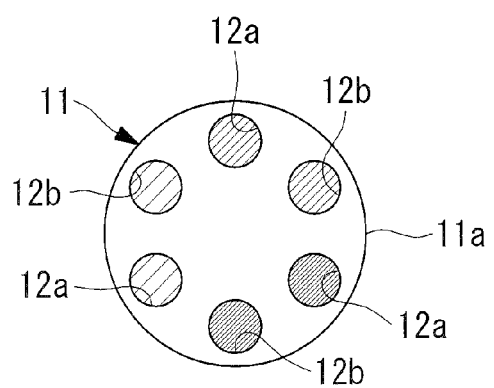
FIG. 5A is a lateral sectional view of a fifth modification of the multi-lumen tube in FIG. 4A showing a case in which a pair of wires are disposed at adjacent positions.
Figure 5B:
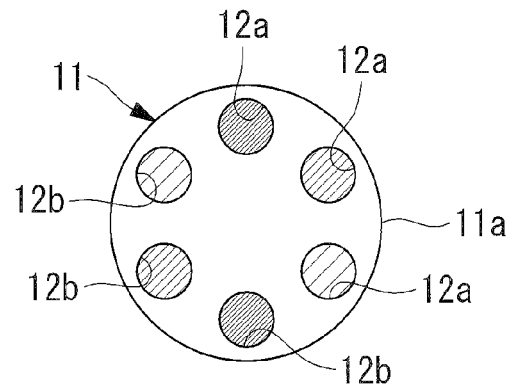
FIG. 5B is a lateral sectional view of the multi-lumen tube in FIG. 5A showing a case in which the pair of wires are disposed at positions symmetrical with respect to a center axis.

In addition, two lumens 12a and 12b that form a pair may be provided in multiple pairs, for example, three pairs, as shown in FIGS. 5A and 5B.

Figure 5C:
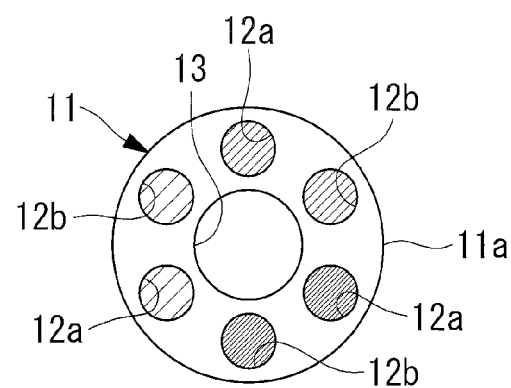
FIG. 5C is a lateral sectional view showing a case in which the multi-lumen tube in FIG. 5A has a lumen at the center.
Figure 5D:
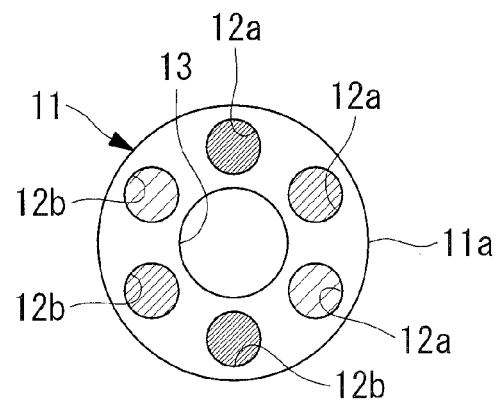
FIG. 5D is a lateral sectional view showing a case in which the multi-lumen tube in FIG. 5B has a lumen at the center.

In this case, a pair of two wires 10 that work together to actuate the same joint or treatment tool may pass through the lumens 12a and 12b adjacently disposed in the circumferential direction, as shown in FIG. 5A, or such wires 10 may pass through the lumens 12a and 12b disposed at positions symmetrical with respect to the center axis of the multi-lumen tube 11a, as shown in FIG. 5B. In these figures, the lumens 12a and 12b through which the wires 10 that work together pass are indicated by the same type of hatching. FIGS. 5C and 5D show multi-lumen tubes 11a in which the other lumens 13 are provided at the centers of the multi-lumen tubes 11a in FIGS. 5A and 5B, respectively.

Figure 6:
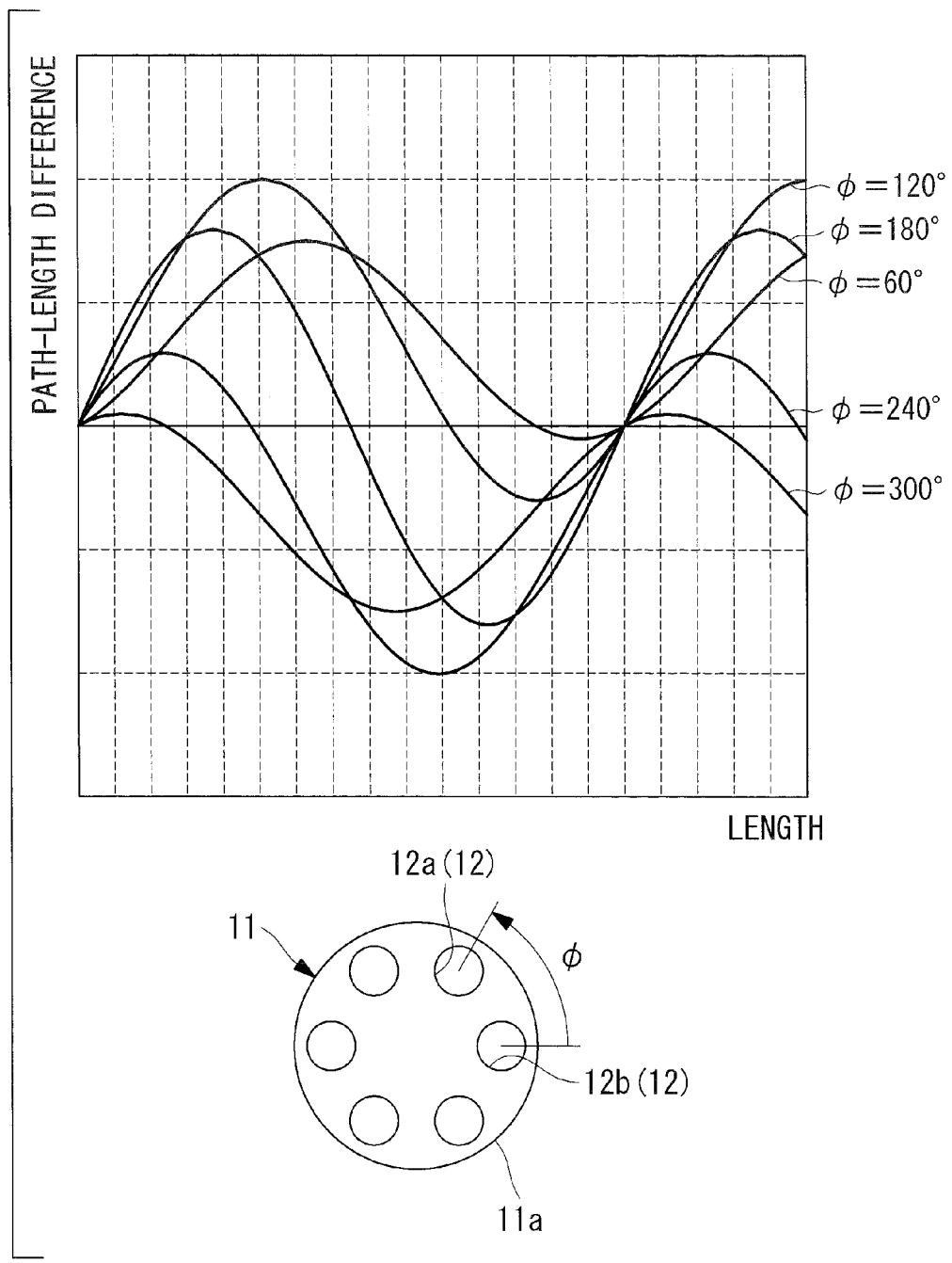
FIG. 6 is a graph for the multi-lumen tube in FIG. 5A showing the relationship between the length of the multi-lumen tube and the path-length differences when the relative angle of two lumens is a parameter.

FIG. 6 is a graph showing the relationship between the arrangement of the two lumens 12a and 12b and the path-length difference between the two lumens 12a and 12b when the multi-lumen tube 11a is bent. The horizontal axis indicates the length of the multi-lumen tube 11a and the vertical axis indicates the path-length difference between the two lumens 12a and 12b. In addition, the parameter is the relative angle φ between the two lumens 12a and 12b in the lateral sectional view shown below the graph. The diagram shows a case in which, for the spiral-shaped lumens 12a and 12b, the spiral radius r=1 mm, the spiral pitch l=150 mm, and the radius of curvature R=60 mm for the bending of the multi-lumen tube 11a.

This case is desirable because the path-length difference due to bending can be kept smaller with a decrease in the relative angle between the two lumens 12a and 12b.

Figure 7A:
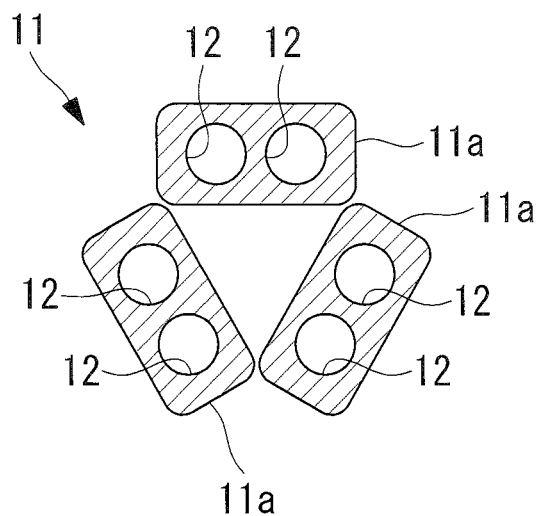
FIG. 7A is a lateral sectional view showing an example in which three of the multi-lumen tubes in FIG. 4B are disposed in the circumferential direction and twisted in a spiraling manner.

In this case, as shown in FIG. 7A, a plurality of, for example, three, multi-lumen tubes 11a whose transverse cross-sectional areas are relatively small and that have the two lumens 12 as shown in FIG. 4B may be arranged in the circumferential direction.

Figure 7B:
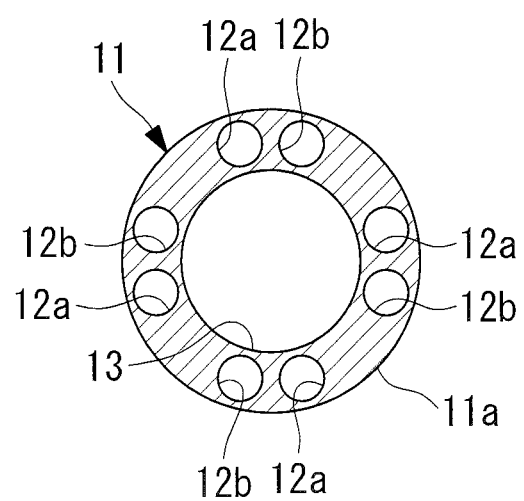
FIG. 7B is a lateral sectional view showing a modification of the multi-lumen tube that has a straight center lumen and four pairs of eight lumens that are positioned outward in the circumferential direction from the center lumen and that are twisted in a spiraling manner.

In addition, as shown in FIG. 7B, multiple pairs of, for example, four pairs, the lumens 12a and 12b may be arranged in the circumferential direction with a space therebetween.

Figure 8A:
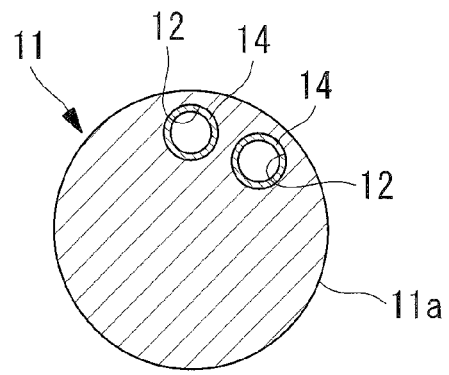
FIG. 8A is a lateral sectional view of the multi-lumen tube that has inner sheaths inside lumens.
Figure 8B:
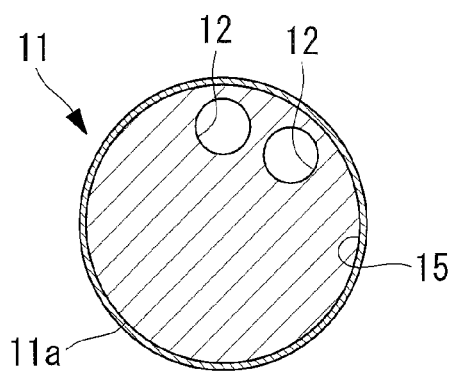
FIG. 8B is a lateral sectional view of the multi-lumen tube that has an outer sheath that covers the exterior thereof.
Figure 8C:
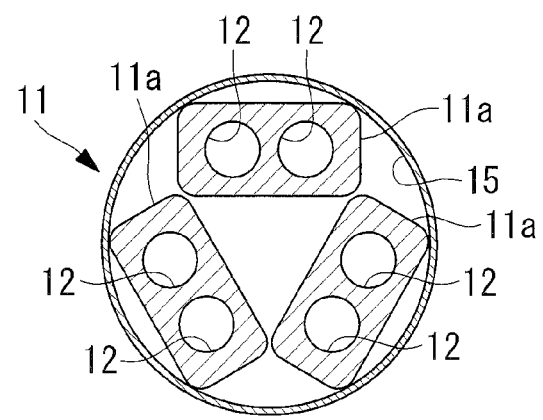
FIG. 8C is a lateral sectional view of the multi-lumen tube in FIG. 7A that has an outer sheath that covers the exterior thereof.

In addition, separate inner sheaths 14 may be disposed inside the lumens 12, as shown in FIG. 8A, or the outer surface of the multi-lumen tube 11a may be covered with a separate outer sheath 15, as shown in FIGS. 8B and 8C.

Figure 9:
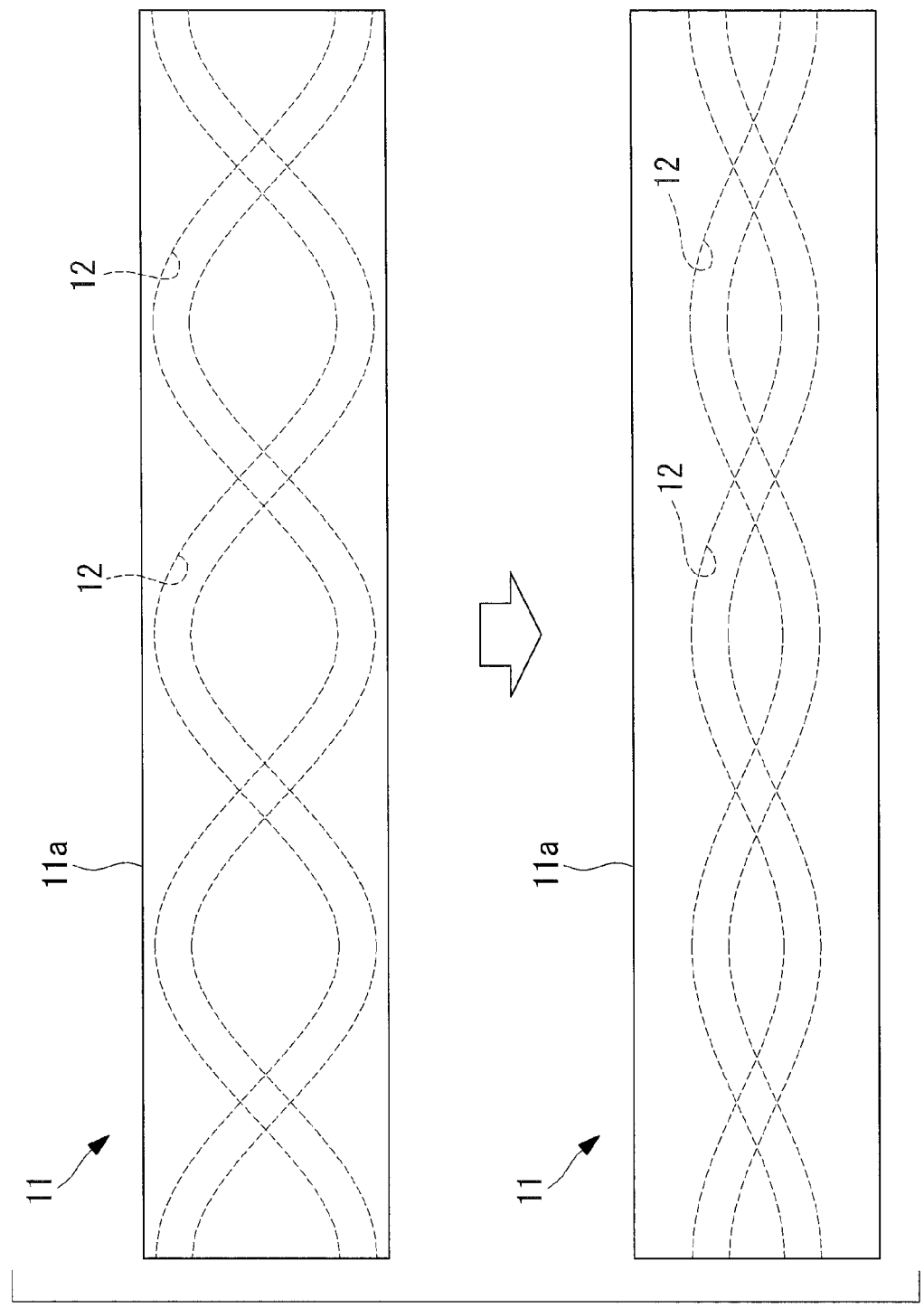
FIG. 9 is a side view for explaining radial positions of the lumens of the multi-lumen tube.

In addition, with regard to the positions of the lumens 12 in the multi-lumen tube 11a in the radial direction thereof, as compared with arranging the lumens 12 radially outward in the multi-lumen tube 11a, as shown in FIG. 9, it is preferable to arrange the lumens 12 in the vicinity of the center axis. By doing so, it is possible to further reduce the changes in the path lengths of the lumens 12 when the inserted portion 6 is bent.

Figure 10:
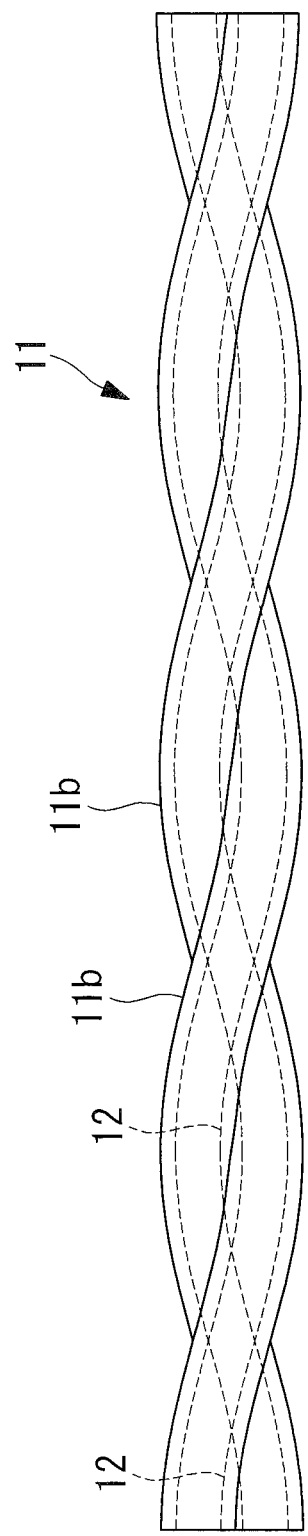
FIG. 10 is a side view showing a twisted-pair multi-lumen tube in which two sheaths having one lumen each are twisted into a single piece.

In addition, it is permissible to employ a multi-lumen tube 11b having a form like a twisted-pair cable that is integrally molded by twisting two lumens 12 that form a pair in a spiraling manner with each other, as shown in FIG. 10, or it is permissible to additionally dispose such a multi-lumen tube 11b about the longitudinal axis of the inserted portion 6 in a spiraling manner.

In addition, three or more lumens 12 may be formed in a braded state instead of a spiral shape. Although it is difficult to manufacture the multi-lumen tube 11a having the braded-state lumens 12 by means of extrusion, manufacturing thereof is possible by using a 3D printer or the like.

Figure 11:
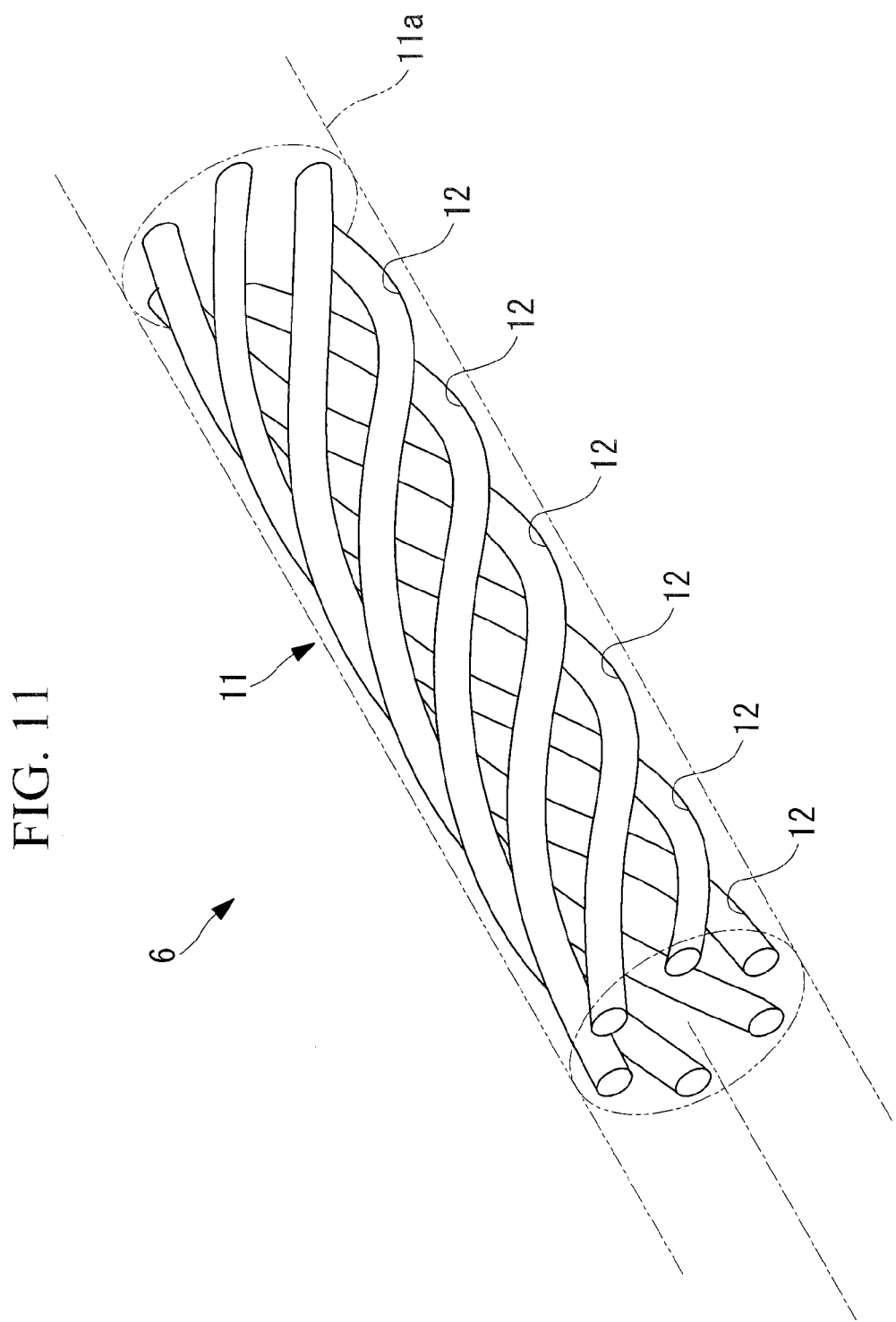
FIG. 11 is a perspective view showing a portion of a multi-lumen tube having six lumens.
Figure 12A:
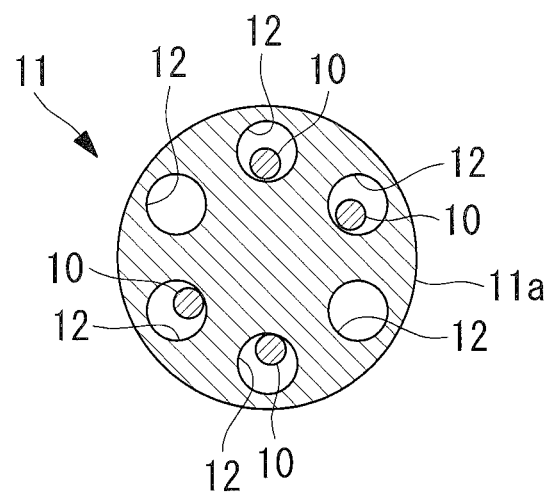
FIG. 12A is a lateral sectional view of a multi-lumen tube in which wires are disposed only in four of six lumens.

In addition, when using the multi-lumen tube 11a having a plurality of, for example, six, lumens 12, as shown in FIG. 11, some of those lumens 12 may be used for other purposes without making the wires 10 pass therethrough, as shown in FIG. 12A. For example, in the case in which a treatment tool is inserted into the forceps channel of the endoscope, the outer diameter of the inserted portion of the treatment tool is slightly decreased, and suction, irrigation, or the like is performed through the clearance with respect to an inner wall of the forceps channel.

In the case in which the treatment tool has a joint or the like, although it is preferable that the outer diameter of the inserted portion of the treatment tool be greater even slightly, a decrease in the clearance causes a performance deterioration with respect to suction or irrigation. Therefore, by performing suction, irrigation, or the like by using the unused lumens 12, there is an advantage in that it is possible to enhance the performance with respect to suction or irrigation while ensuring a large enough treatment-tool diameter.

Figure 12B:
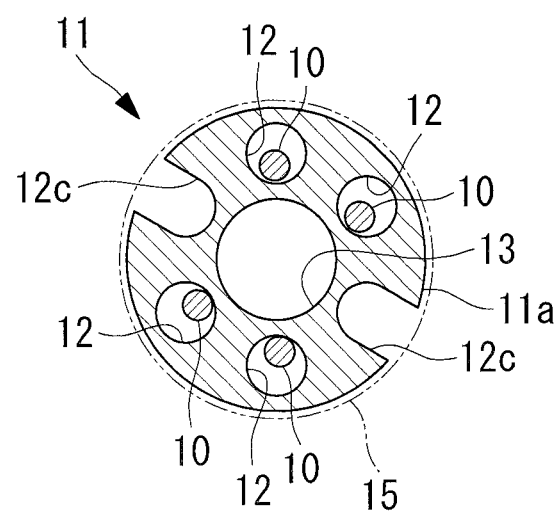
FIG. 12B is a lateral sectional view of a multi-lumen tube in which wires are disposed only in four of six lumens and in which the remaining two lumens are formed like grooves that open at outer surfaces.

In addition, in this case, as shown in FIG. 12B, portions of the unused lumens 12c may be formed like grooves that open at outer surfaces of the multi-lumen tube 11a. By doing so, even if the above-described clearance is decreased, it is possible to ensure a large enough channel area for a fluid and, also, the area in which contact is made with the inner surface of the forceps channel is decreased by amounts corresponding to the widths of the grooves (through-paths) 12c.

In other words, there is an advantage in that it is possible to enhance the maneuverability by decreasing the friction while accurately transmitting the amount of movement of the inserted portion of the treatment tool by decreasing the clearance.

Here, by using polyether ether ketone (PEEK) as the material for the multi-lumen tube 11a, it is possible to form an inserted portion 6 that has a high rigidity and with which the lumens 12 in the interior thereof do not collapse due to bending. Alternatively, from the viewpoint of the costs and the ease of manufacturing, a soft material, such as tetrafluoroethylene resin or the like may be selected.

However, in this case, because it is conceivable that the multi-lumen tube 11a becomes compressed in the longitudinal direction due to a compression force when the tensile forces in the wires 10 passing through inside the lumens 12 are increased, the inner sheaths 14 shown in FIG. 8A or the outer sheaths 15 shown in FIGS. 8B and 8C may be used, or both may be used in combination. With regard to the material for the inner sheaths 14 or the outer sheaths 15, metal-based (stainless steel and nickel titanium) pipes or coils, or PEEK or polyetherimide (PEI) resin may be used. In addition, these sheaths 14 and 15 and the multi-lumen tube 11a may be glued together.

An adhesive to be applied between the outer sheath 15 and the multi-lumen tube 11a may be applied over the entire surface so as to resist a large tensile force, or the adhesive may be applied in a spiraling manner or may be applied in blotches so as to achieve both flexibility and compression resistance.

Next, the pitch of the spiral shape of the lumens 12 will be described.

Although changes in the relative path-lengths of the two wires 10 forming a pair are decreased regardless of the bending state of the inserted portion 6 when the spiral pitch is decreased, making the pitch increasingly smaller increases the friction when the inserted portion 6 is in the straight state. Therefore, with regard to the trade-off relationship between pitch and friction, an appropriate pitch is determined by using theoretical expressions.

When it is assumed that the ratio of the spiral path length $l_t$ to the pitch l of the inserted portion 6 is a, the radius of curvature of the inserted portion 6 is R, the relative path-length difference of the wires 10 is $dL_R$, the spiral pitch is l, and the spiral radius is r, it is preferable that the following conditional expression (1) be satisfied.

$$2\pi r/\sqrt{(a^2-1)} \leq l \leq 6.25 R dL_R/r \quad (1)$$

For example, when a is 1.1, the radius of curvature R=60 for the inserted portion 6, and r=2 for a treatment tool whose diameter is 5 mm:

$$27.4 \leq l \leq 375.$$

The conditional expression (1) can be derived as follows. The coordinates from the origin for the radius of curvature R are as expressed by Eq. 1.

$$\begin{pmatrix} x \\ y \\ z \end{pmatrix} = \begin{pmatrix} r\cos\left(\frac{2\pi}{l}s+\phi\right)\cos\left(\frac{1}{R}s\right) + R\left\{1-\cos\left(\frac{1}{R}s\right)\right\} \\ r\sin\left(\frac{2\pi}{l}s+\phi\right) \\ -r\cos\left(\frac{2\pi}{l}s+\phi\right)\sin\left(\frac{1}{R}s\right) + R\sin\left(\frac{1}{R}s\right) \end{pmatrix} \quad \{\text{Eq. 1}\}$$

In addition, the spiral path length L is as expressed by Eq. 2.

$$L = \int_0^L \sqrt{\left(\frac{dx}{ds}\right)^2 + \left(\frac{dy}{ds}\right)^2 + \left(\frac{dz}{ds}\right)^2} \quad \{\text{Eq. 2}\}$$

The maximum path-length change (amplitude) $dL_R$ when flexing with the radius of curvature R from the straight state is:

$$dL_R = krl/R \quad (2).$$

Here, k is a constant (=0.16).

This conditional expression (2) indicates that the maximum path-length change is proportional to the inverse of the radius of curvature R, is proportional to the spiral pitch l, and is proportional to the spiral radius r.

Determining the relationship between the spiral radius r and the spiral pitch l from conditional expression (2) gives:

$$rl = RdL_R/0.16.$$

In order to make the relative path-length difference of the wires 10 equal to or less than $dL_R$, $$rl \leq 6.25 R dL_R.$$

By using this, the upper limit of conditional expression (1) is determined.

Accordingly, in order to make the radius of curvature R=60 and the relative path-length difference of the wires 10 equal to or less than 2 mm, $$rl \leq 750.$$

In addition, calculating the radius of curvature $R_t$ of a spiral path from the expression for a spiral shown in Eq. 3 gives Eq. 4.

$$\begin{pmatrix} x \\ y \\ z \end{pmatrix} = \begin{pmatrix} r_c \cos\left(\frac{2\pi}{l}s+\phi\right) \\ r_c \sin\left(\frac{2\pi}{l}s+\phi\right) \\ s \end{pmatrix} \quad \{\text{Eq. 3}\}$$

$$R_t = \frac{4\pi^2 r_c^2 + l^2}{4\pi^2 r} \quad \{\text{Eq. 4}\}$$

Here, $r_c$ is the spiral radius at points of contact between the wires 10 and the lumens 12.

Figure 13:
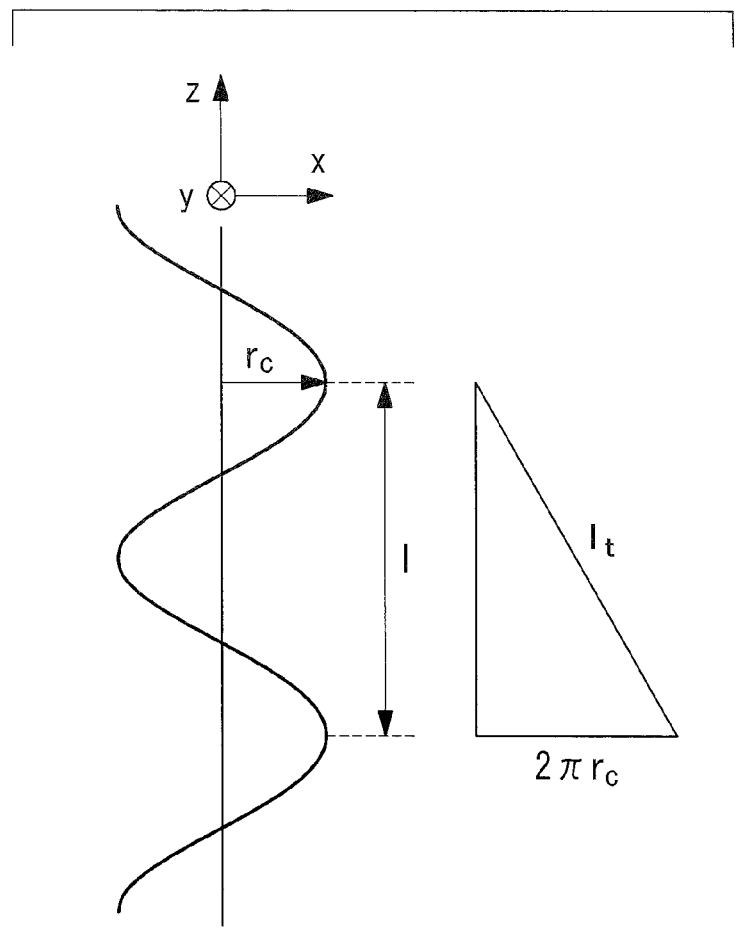
FIG. 13 is a diagram for explaining the relationship between the spiral path length and the length of the multi-lumen tube.

Because the spiral path length $l_t$ for one pitch is equal to the length of a path when the path is expanded as in FIG. 13, $$l_t = \sqrt{(4\pi^2 r_c^2 + l^2)}.$$

Figure 14:
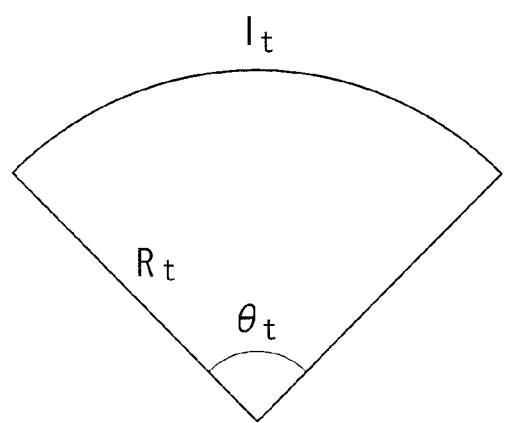
FIG. 14 is a diagram for explaining the flexing angle of the spiral lumen.

Thus, from the radius of curvature $R_t$ and the spiral path length $l_t$ for one pitch, the flexing angle $\theta_t$ for one pitch for the wire 10 as in FIG. 14 can be determined from the expression below.

$$\theta_t = l_t/R_t$$

The flexing angle $\theta_{ta}$ for the wire 10 for the overall spiral path length L is:

$$\theta_{ta} = \theta_t L/l.$$

Euler's formula below holds between a tensile force $T_1$ exerted on the base end of the wire 10 and a tensile force $T_2$ at the distal end of the wire 10.

$$T_1 = T_2 e^{\mu \theta_{ta}}$$

Here, μ is the coefficient of friction.
The frictional force F is:

$$F = T_1 - T_2.$$

In order to suppress the frictional force to b times as great as the tensile force, the pitch l needs to satisfy Eq. 5.

$$l > \sqrt{2}\,\pi r_c \sqrt{\sqrt{1 + \frac{4\mu^2 L^2}{r_c^2 \{\log_e(1+b)\}^2}} - 1} \quad \{\text{Eq. 5}\}$$

Table 1 shows the pitch l when various conditions are changed.

TABLE 1

| $r_c$ | L | μ | b | l |
|---|---|---|---|---|
| 0.5 | 2000 | 0.02 | 0.15 | 75.1 |
| 0.5 | 2000 | 0.05 | 0.15 | 118.8 |
| 0.5 | 2000 | 0.02 | 0.3 | 54.8 |
| 0.5 | 2000 | 0.05 | 0.3 | 86.7 |
| 0.5 | 3000 | 0.02 | 0.15 | 92.0 |
| 0.5 | 3000 | 0.05 | 0.15 | 145.5 |
| 0.5 | 3000 | 0.02 | 0.3 | 67.2 |
| 0.5 | 3000 | 0.05 | 0.3 | 106.2 |
| 0.65 | 2000 | 0.02 | 0.15 | 85.6 |
| 0.65 | 2000 | 0.02 | 0.3 | 62.5 |
| 1.1 | 2000 | 0.02 | 0.15 | 111.4 |
| 1.1 | 2000 | 0.02 | 0.3 | 81.2 |

According to this, assuming that the length of the inserted portion 6 is 2 m, it is necessary to make the pitch l equal to or greater than 50 mm in order to suppress the friction to 30% or less of the tensile force, and it is necessary to make the pitch l equal to or greater than 75 mm in order to suppress the friction to 15% or less of the tensile force.

It is also clear that, assuming that the length of the inserted portion 6 is 3 m, it is necessary to make the pitch l equal to or greater than 60 mm in order to suppress the friction to 30% or less of the tensile force, and that it is necessary to make the pitch l equal to or greater than 90 mm in order to suppress the friction to 15% or less of the tensile force.

Because stretching of the wires 10 is proportional to the lengths of the wires 10, increasing the path lengths promotes stretching of the wires 10, and thus, the controllability or the maneuverability is deteriorated. Therefore, by restricting the lengths of the wires 10 when employing the spiral lumens 12 relative to those when employing the straight lumens 12, it is possible to restrict stretching of the wires 10, and it is possible to guarantee the controllability or the maneuverability.

Specifically, by using the ratio a of the spiral path length $l_t$ and the pitch l of the inserted portion 6, the following relational expression holds:

$$l/r=2\pi/\sqrt{(a^2-1)}.$$

Therefore, in order to make the ratio of the spiral path length $l_t$ to the pitch l equal to or less than a, $$l/r\geq 2\pi/\sqrt{(a^2-1)}$$

holds. By using this, the lower limit of conditional expression (1) is determined.

According to this, in order to make the ratio a of the spiral path length $l_t$ to the pitch l equal to or less than 1.1, in other words, in order to make stretching of the wires 10 in the case in which the wires 10 pass through the spiral lumens 12 equal to or less than 10% of stretching of the wires 10 in the case in which the wires 10 pass through the straight lumens 12, $$l/r\geq 13.7$$

holds.

In addition, in order to make stretching of the wires 10 in the case in which the wires 10 pass through the spiral lumens 12 equal to or less than 5% of stretching of the wires 10 in the case in which the wires 10 pass through the straight lumens 12, $$l/r\geq 19.6$$

holds.

Figure 15:
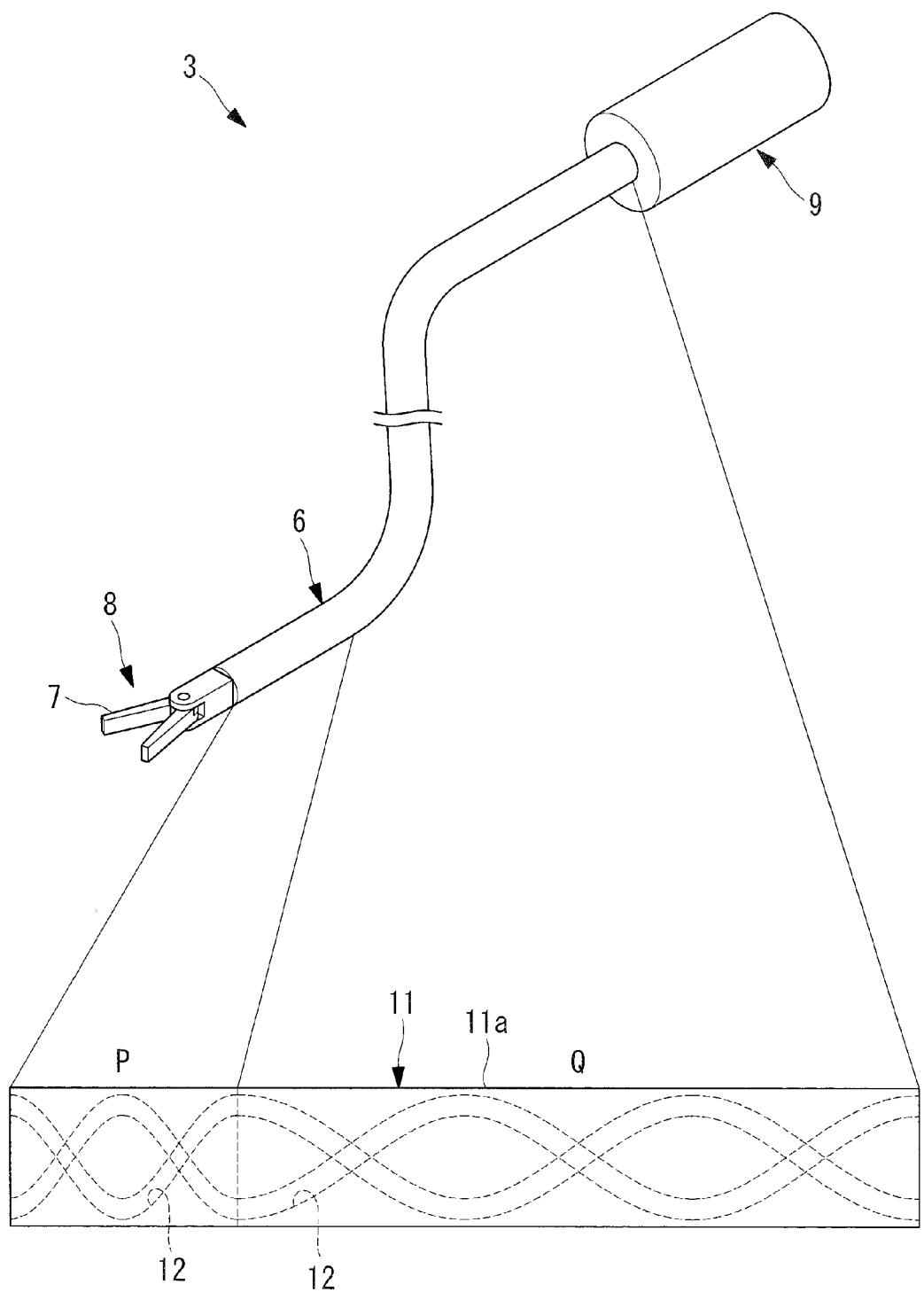
FIG. 15 is a diagram for explaining a case in which pitches of the spiral shapes of the lumens differ in the longitudinal direction of the inserted portion.

In addition, in this embodiment, although a case in which the lumens 12 have a constant spiral shape over the entire length thereof has been described, alternatively, as shown in FIG. 15, a spiral shape having different pitches in the length direction of the inserted portion 6 may be formed. In the example shown in FIG. 15, the spiral pitch is decreased for a portion P that corresponds to a bending portion of the endoscope, in which the flexible manipulator 3 according to this embodiment passes through the forceps channel thereof, and that is bent by the bending portion, and the spiral pitch is increased for a portion Q other than the portion P.

By doing so, as for the portion P, it is possible to make a path-length difference less likely to occur even if the portion P is flexed by a large curvature, whereas, as for the portion Q, it is possible to decrease the friction generation by increasing the pitch because the portion Q is flexed with a relatively small curvature.

Figure 16:
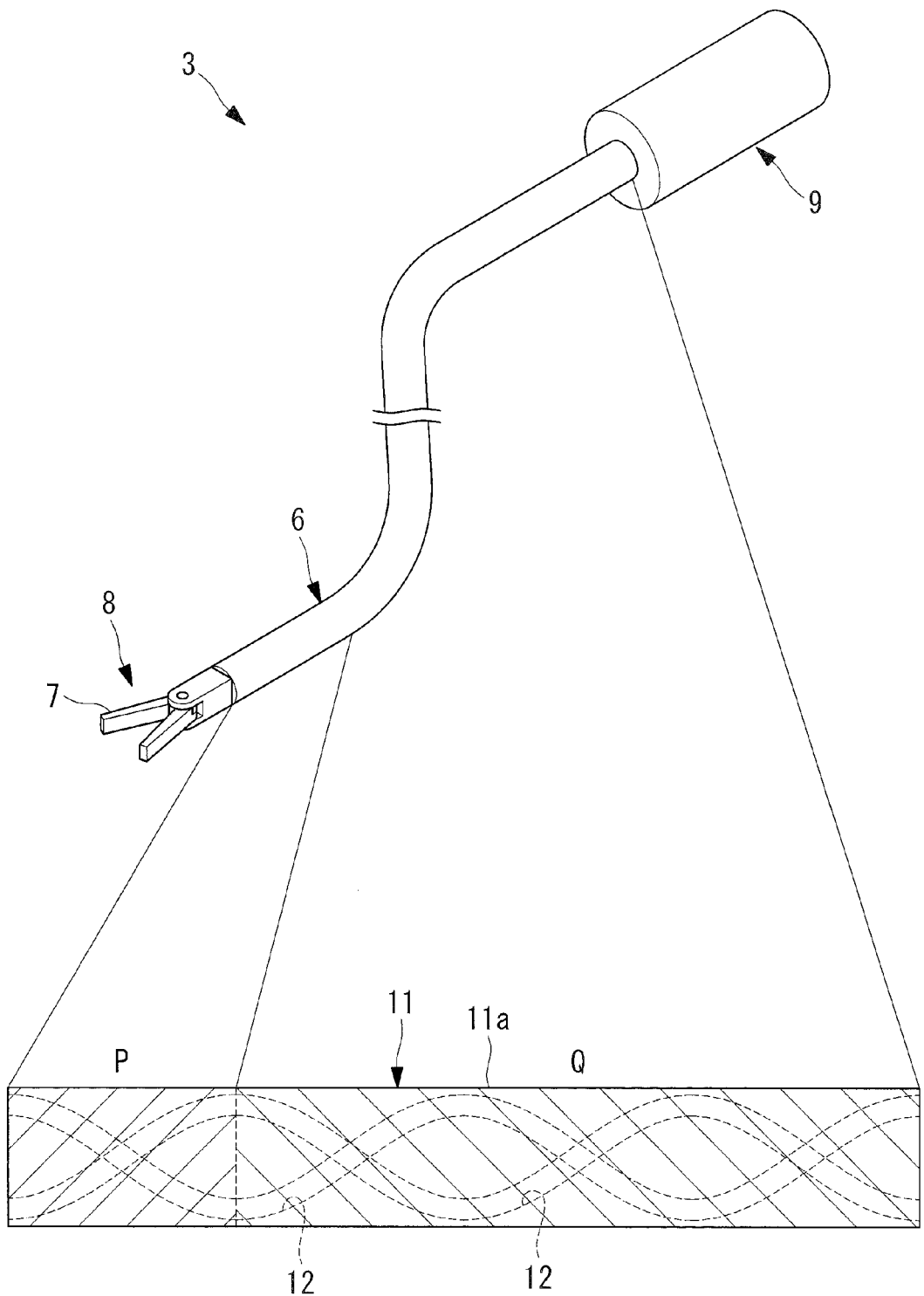
FIG. 16 is a diagram for explaining a case in which materials of the lumens differ in the longitudinal direction of the inserted portion.

In addition, in this embodiment, although a case in which the multi-lumen tube 11a is formed of a uniform material over the entire length thereof has been described, alternatively, as shown in FIG. 16, portions P and Q formed of different materials may be made continuous in the length direction of the inserted portion 6. For example, a material having a low flexural rigidity may be used for the portion P, which is bent by the bending portion, in order to impart a greater flexibility and to facilitate bending thereof as compared with the portion Q other than the portion P, and the portion Q can be prevented from collapsing due to compression by securing the multi-lumen tube 11a to the movable portion 8 at the distal end thereof. In addition, as for the portion Q, it is preferable to apply a material having a high compression resistance.

Figure 17:
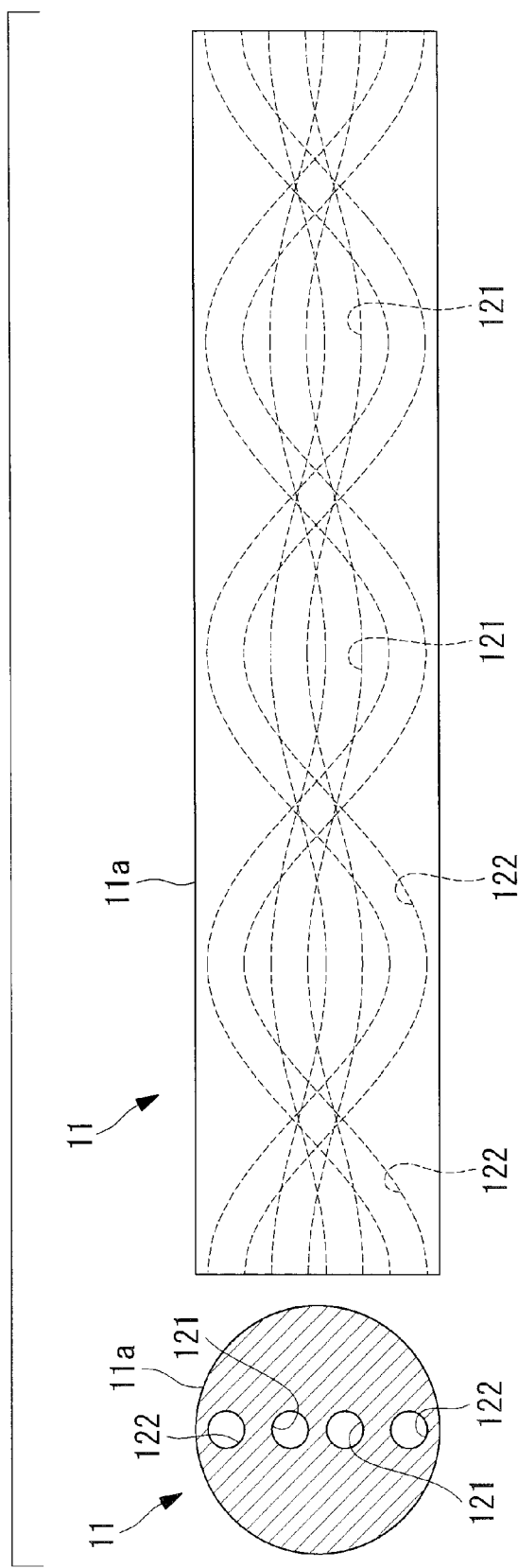
FIG. 17 is a front view and a side view showing a case in which the lumens are provided at different positions in the radial direction of the inserted portion.

In addition, as shown in FIG. 17, lumens 121 and 122 may be disposed at different positions in the radial direction in the multi-lumen tube 11a. For example, in the case in which the movable portion 8 provided at the distal end of the inserted portion 6 has a plurality of joints, grippers (treatment portions) 7, or the like, and tensile forces required for the wires 10 to drive the individual components are different, the wire 10 for which a greater tensile force is required can be made to pass through the lumen 121 which is positioned radially inward where the path-length difference due to bending is smaller. By doing so, with regard to the wire 10 that passes through the lumen 121 positioned radially inward, an increase in the friction due to bending is suppressed, and thus, it is possible to enhance the maneuverability or the controllability.

Figure 18:
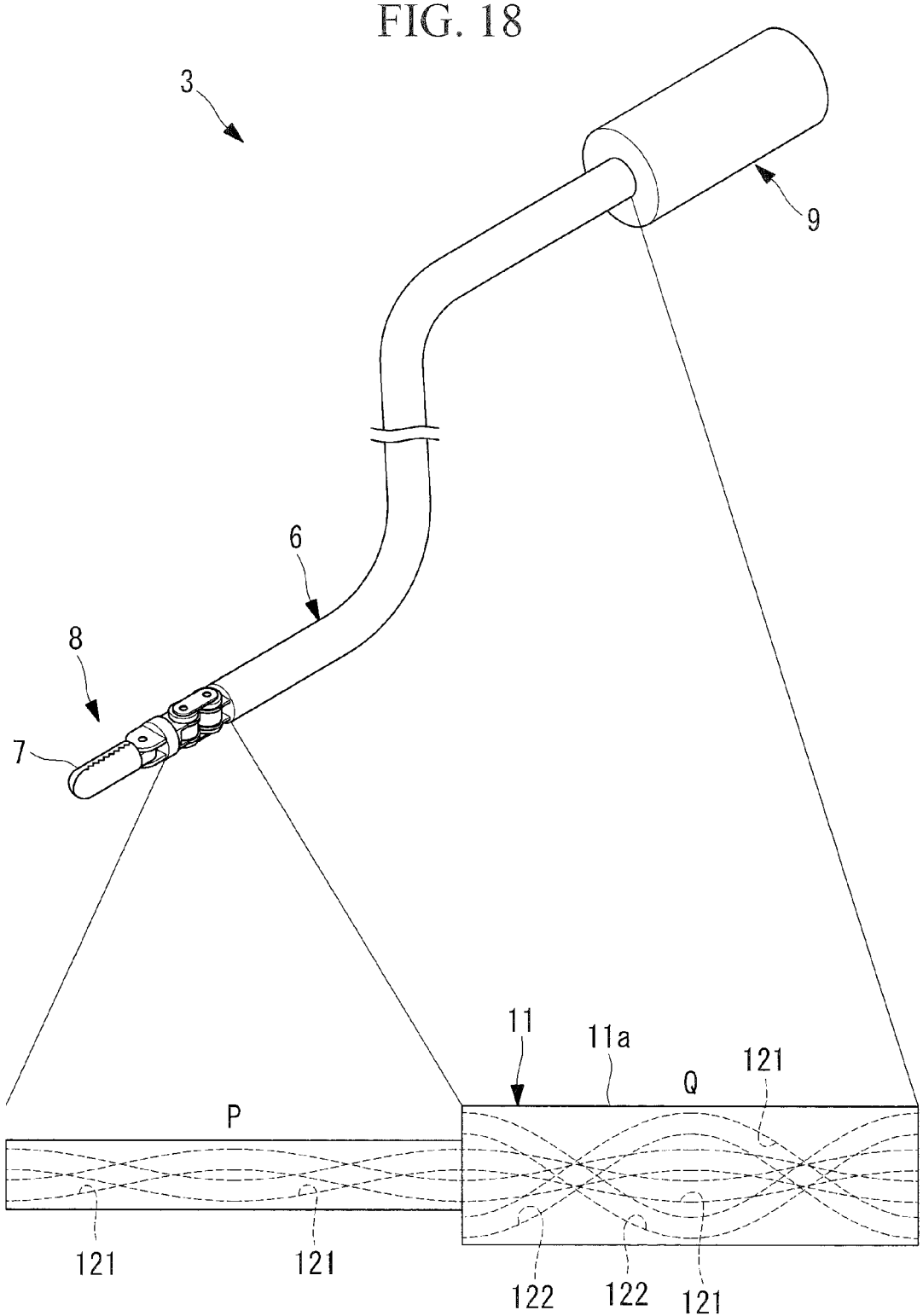
FIG. 18 is a diagram for explaining a multi-lumen tube in which the outer diameters differ in the longitudinal direction of the inserted portion.

In addition, as shown in FIG. 18, in the case in which grippers 7 or the like at the distal ends of a plurality of joints are included as the movable portion 8, because the wires 10 for driving the grippers 7 need to pass through inside the joints, with regard to the portion P that passes through the joints, the flexural rigidity may be decreased by decreasing the outer diameter of the multi-lumen tube 11a as compared with the portion Q other than the portion P.

Figure 19A:
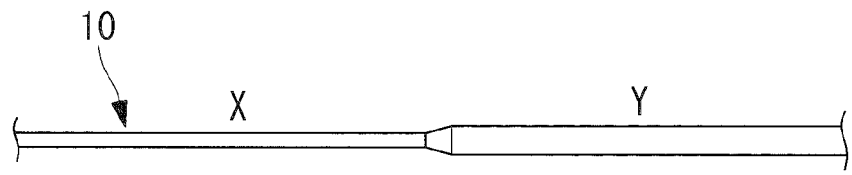
FIG. 19A is a side view showing a portion of a wire having a shape in which portions having different outer diameters are connected in the longitudinal direction.
Figure 19B:
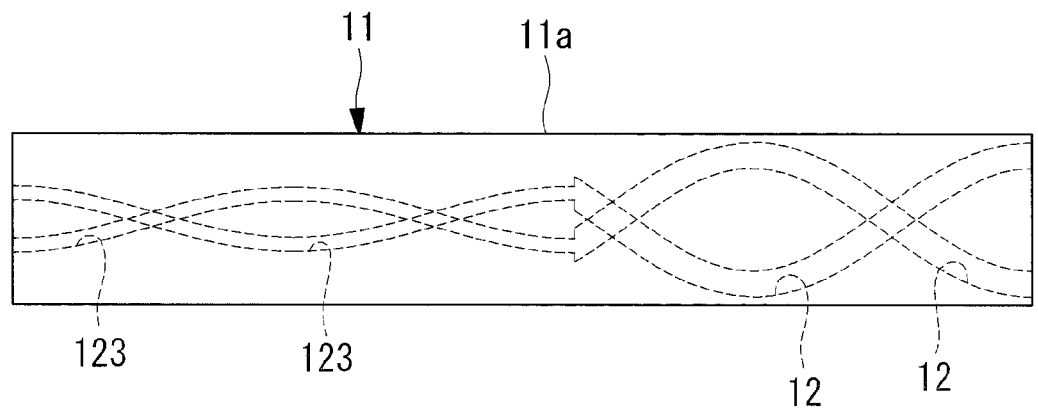
FIG. 19B is a side view of an example of a multi-lumen tube through which the wire in FIG. 19A passes.

In addition, as shown in FIG. 19A, the wires 10 whose diameters change at intermediate positions in the longitudinal direction are used in some cases. For example, with regard to a portion X that is at the distal end of the inserted portion 6 and that is bent by a large curvature, there are cases in which the wire 10 is also made thinner so as to facilitate flexing as compared with a portion Y other than the portion X. In such a case, the inner diameters of the lumens 12 may be changed at intermediate positions, as shown in FIG. 19B, in order to decrease the clearances between the wires 10 and lumens 123 through which the thin wires 10 pass.

Figure 20:
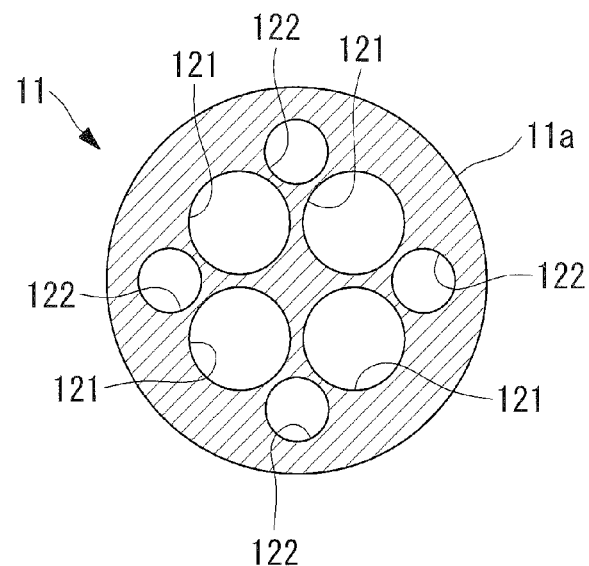
FIG. 20 is a lateral sectional view showing another modification of the multi-lumen tube in FIG. 4A.

In addition, as shown in FIG. 20, the wires 10 for which friction needs to be decreased may pass through lumens 121 positioned radially inward, and electric cables or the like other than those wires 10 may be disposed in lumens 122 positioned radially outward.

Figure 21:
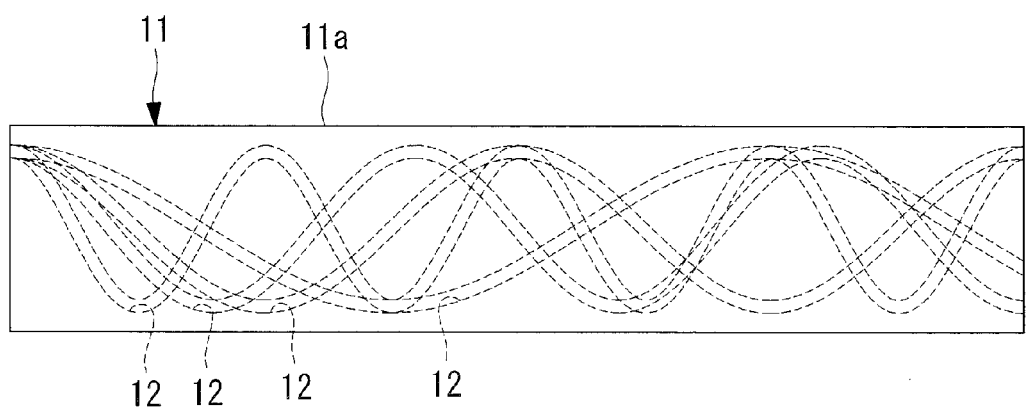
FIG. 21 is a side view showing a multi-lumen tube having a plurality of lumens in which pitches of the spiral shapes thereof are different.

In addition, in this embodiment, although a case in which all lumens 12 are twisted in a spiraling manner at the same pitch has been described as an example, pitches of the individual lumens 12 may be different, as shown in FIG. 21.

By doing so, it is possible to select appropriate lumens 12 in accordance with tolerable flexing radii of the wires 10, optical fibers, electric cables, or the like that pass through the lumens 12.

In addition, as shown in FIGS. 22A and 22B, a flexible treatment tool may pass through a through-hole 13 at the center of the multi-lumen tube 11a, a distal-end portion of the low-rigidity multi-lumen tube 11a may be made to protrude from the distal end of the high-rigidity outer sheath 15, and the multi-lumen tube 11a at the protruded portion may be bent by means of the tensile forces in the wires 10 disposed inside the lumens 12. The distal ends of the wires 10 can be secured to a plate 16 provided at the distal end of the multi-lumen tube 11a.

In addition, in this embodiment, the drive portion 9 may be driven by a motor, or the drive portion 9 may be driven by manual manipulation.

In addition, although the medical flexible manipulator 3 that is inserted into the body cavity of the patient O has been described as an example, the present invention is not limited thereto, and it may be applied to a snake-type long manipulator including an industrial endoscope.

From the above-described embodiments and modifications thereof, the following aspects of the invention are derived.

An aspect of the present invention is a flexible-manipulator guide member that is provided in an inserted portion of a flexible manipulator equipped with the elongated flexible inserted portion; a movable portion disposed at a distal end of the inserted portion; a drive portion disposed at a base end of the inserted portion; and an elongated driving-force transmitting member that transmits motive power of the drive portion to the movable portion, the flexible-manipulator guide member including a lumen through which the driving-force transmitting member passes in a longitudinal direction thereof, wherein the lumen has a twisted shape about a longitudinal axis of the inserted portion.

With this aspect, when the drive portion disposed at the base end of the inserted portion is actuated, the generated motive power is transmitted to the movable portion disposed at the distal end of the inserted portion by the driving-force transmitting member that passes through inside the lumen, thus actuating the movable portion. When the elongated flexible inserted portion is bent, although the shape of the lumen is also changed with the bending thereof, the contact state between the inner surface of the lumen having the twisted shape about the longitudinal axis of the inserted portion and the driving-force transmitting member passing through inside the lumen does not greatly change depending on the bending state of the inserted portion, and thus, there is no need to greatly change the motive power generated by the drive portion depending on the bending state. Therefore, it is possible to enhance the maneuverability or the controllability of the movable portion.

In the above-described aspect, the lumen may be formed in a spiral shape.

By doing so, with the spiral lumen having a uniform pitch, it is possible to exhibit uniform performance at respective portions of the inserted portion, and it is also possible to enhance the ease of manufacturing. In addition, by decreasing the pitch of the spiral shape, the contact state between the inner surface of the lumen and the driving-force transmitting member does not change even if the inserted portion is bent to have a greater curvature.

In addition, in the above-described aspect, the lumen may satisfy the following conditional expression:

$$2\pi r/\sqrt{(a^2-1)} \leq l \leq 6.25 R d L_R/r,$$

where, R is the radius of curvature of the inserted portion, r is the radius of the spiral shape, l is the pitch of the spiral shape, $dL_R$ is the maximum tolerance of the driving-force transmitting member with respect to the relative path-length difference, and a is the maximum tolerance of a ratio of the path length of the spiral shape to the pitch of the inserted portion.

By doing so, it is possible to suppress the change in the path length of the driving-force transmitting member to equal to or less than 2 mm when the flexing radius of the inserted portion is 60 mm. In addition, as compared with a case in which the shape of the lumen is straight, stretching of the driving-force transmitting member can be suppressed to 10% or less.

In addition, in the above-described aspect, the pitches of the spiral shape of the lumen may differ at respective positions in the longitudinal direction of the inserted portion.

By doing so, at a portion in which flexing by a large curvature is necessary, the change in the contact state between the inner surface of the lumen and the driving-force transmitting member can be suppressed by decreasing the pitches of the spiral shape of the lumen, and, at a portion in which flexing by a small curvature is tolerated, it is possible to suppress the deterioration of the controllability due to stretching of the driving-force transmitting member by decreasing the path length.

In addition, in the above-described aspect, two or more of the lumens may be provided.

By doing so, it is possible to drive two or more movable portions or to perform reciprocating motion of the movable portion by using the driving-force transmitting members guided by separate lumens. Thus, when the inserted portion is bent, the relative path-length difference generated between two or more driving-force transmitting members passing through two or more lumens can be suppressed to a low value.

In addition, in the above-described aspect, a plurality of pairs of the lumens may be provided and the two lumens of each pair may be disposed next to each other.

By doing so, because the two lumens in the respective pairs are made to have similar paths, when the inserted portion is bent, the relative path-length difference generated between the two lumens in the respective pairs can be suppressed to a low value.

In addition, two or more of the lumens may be provided, and the pitches of the spiral shapes of the individual lumens may differ from each other.

By doing so, it is possible to select appropriate lumens and to arrange them by means of insertion in accordance with the tolerable flexing radii of the driving-force transmitting members or the like that pass through inside the lumens.

Another aspect of the present invention is a flexible-manipulator guide member that is provided in an inserted portion of a flexible manipulator equipped with the elongated flexible inserted portion; a movable portion disposed at a distal end of the inserted portion; a drive portion disposed at a base end of the inserted portion; and elongated driving-force transmitting members that transmit motive power of the drive portion to the movable portion, the flexible-manipulator guide member including three or more lumens through which the driving-force transmitting members pass in longitudinal directions thereof, wherein the lumens have a braided shape along the longitudinal axis of the inserted portion.

With this aspect, as with the case in which the lumens are formed in a spiral shape, when the elongated flexible inserted portion is bent, the contact state with the driving-force transmitting members passing through inside the lumens does not change, and thus, there is no need to greatly change the motive power generated by the drive portion depending on the bending state. Therefore, it is possible to enhance the maneuverability or the controllability of the movable portion.

In addition, in the above-described aspect, the multiple lumens may be provided at different positions in radial directions.

By doing so, when the inserted portion is bent, the change in the path length of the lumen disposed radially inward can be suppressed to a lower level as compared with that of the lumen disposed radially outward. Therefore, it is possible to enhance the controllability of the movable portion by making the driving-force transmitting member requiring transmission of a greater driving force pass through the lumen disposed radially inward.

In addition, the above-described aspect may be formed of a multi-lumen tube having flexibility.

By doing so, it is possible integrally mold flexible-manipulator guide members that maintain the relative positional relationship of the plurality of paths.

In addition, in the above-described aspect, the flexibilities of the multi-lumen tube may differ at respective positions in the longitudinal direction.

By doing so, by employing a low-flexibility material in a portion of the inserted portion that is bent by a relatively small curvature, it is possible to make the inserted portion firm. In addition, it is possible to enhance the ease of bending by forming a portion that needs to be bent by a large curvature by using a high-flexibility material.

Another aspect of the present invention is a flexible manipulator including an elongated flexible inserted portion; a movable portion disposed at a distal end of the inserted portion; a drive portion disposed at a base end of the inserted portion; an elongated driving-force transmitting member that transmits motive power of the drive portion to the movable portion; and any one of the above-described flexible-manipulator guide members.

With this aspect, the motive power of the drive portion exerted on the base end of the inserted portion is transmitted to the movable portion at the distal end of the inserted portion by the driving-force transmitting member that passes through inside the lumen of the flexible-manipulator guide member, thus actuating the movable portion. Because the flexible-manipulator guide member suppresses a change of friction between the inner surface of the lumen and the driving-force transmitting member before and after bending the inserted portion, it is possible to precisely actuate the movable portion by enhancing the maneuverability exhibited by means of the drive portion or the controllability of the drive portion.

Another aspect of the present invention is a flexible manipulator including an elongated flexible inserted portion; a movable portion disposed at a distal end of the inserted portion; a drive portion disposed at a base end of the inserted portion; an elongated driving-force transmitting member that transmits motive power of the drive portion to the movable portion; and any one of the above-described flexible-manipulator guide members, wherein the flexible-manipulator guide member is provided with, separately from the lumen, a through-path that passes therethrough in the longitudinal direction.

With this aspect, wiring, optical fibers, or other elongated members can pass through or a fluid can flow via the through-path passing through in the longitudinal direction, in addition to the lumen through which the driving-force transmitting member passes. The through-path may be twisted or may not be twisted.

In the above-described aspect, the through-path may be formed of a groove formed in an outer surface of the flexible-manipulator guide member.

By doing so, it is easy to form the through-path, and a relatively large transverse cross-sectional area is ensured, and thus, when making a fluid flow, the fluid can be flow at a large flow volume.

In addition, in the above-described aspect, as compared with the lumen, the through-path is disposed radially farther inward in the flexible-manipulator guide member.

By employing such a configuration, in the case in which an elongated member such as wiring, an optical fiber, or the like passes through the through-path, no restriction is imposed on the flexing direction of the inserted portion.

In addition, in the above-described aspect, the inserted portion may be provided with a flexible outer sheath through which the flexible-manipulator guide member passes in the longitudinal direction.

By doing so, a multi-lumen tube made of a high-flexibility material is used as the flexible-manipulator guide member, a high enough rigidity is ensured by using the outer sheath, and thus, it is possible to prevent buckling or the like of the lumen.

REFERENCE SIGNS LIST 3 flexible manipulator
6 inserted portion
8 movable portion
9 drive portion
10 wire (driving-force transmitting member)
11 flexible-manipulator guide member
12, 12a, 12b, 121, 122, 123 lumen
12c groove (through-path)
13 lumen (through-hole, through-path)
15 outer sheath

The invention claimed is:

1. A manipulator comprising:
a guide extending along a longitudinal axis, wherein the guide comprises:
a lumen inner surface configured to define a lumen extending along the longitudinal axis of the guide,
wherein the lumen comprises a first portion and a second portion along the longitudinal axis, and
wherein at least the first portion of the lumen has a spiral-shape extending along the longitudinal axis; and
a wire arranged within the lumen defined by the lumen inner surface,
wherein the wire is configured to transmit a driving force generated by an actuator to a movable structure, and
wherein the lumen inner surface is configured such that:
a path length of the lumen per unit length of the guide along the longitudinal axis in the first portion of the lumen is different from a path length of the lumen per unit length of the guide along the longitudinal axis in the second portion of the lumen.

2. The manipulator according to claim 1,
wherein the second portion of the lumen has the spiral-shape.

3. The manipulator according to claim 2,
wherein a pitch of the spiral-shape of the first portion of the lumen is different from a pitch of the spiral-shape of the second portion of the lumen.

4. The manipulator according to claim 1,
wherein the guide comprises a multi-lumen tube comprising a plurality of the lumen inner surface, and
wherein the plurality of the lumen inner surface defines a plurality of the lumen.

5. The manipulator according to claim 1,
wherein the guide comprises:
an insertion portion; and
a sheath arranged within the insertion portion, wherein the sheath comprises the lumen inner surface.

6. The manipulator according to claim 1,
wherein the movable structure is a treatment device configured to move to perform a treatment, and
wherein the wire is configured to transmit the driving force generated by the actuator to the treatment device to move the treatment device to perform the treatment.

7. The manipulator according to claim 1,
wherein the guide comprises:
a flexible insertion portion,
wherein the movable structure comprises a connection point of the flexible insertion portion, and
wherein the wire is configured to transmit the driving force generated by the actuator to the connection point of the flexible insertion portion to move at least the connection point of the flexible insertion portion.

8. The manipulator according to claim 1,
wherein the first portion of the lumen is closer to the movable structure than the second portion of the lumen, and
wherein the path length of the lumen per unit length of the guide along the longitudinal axis in the first portion of the lumen is longer than the path length of the lumen per unit length of the guide along the longitudinal axis in the second portion of the lumen.

9. The manipulator according to claim 8,
wherein a length along the longitudinal axis of a first portion of the guide including the first portion of the lumen is shorter than a length along the longitudinal axis of a second portion of the guide including the second portion of the lumen.

10. The manipulator according to claim 1,
wherein the lumen inner surface is configured such that:
in a state in which the actuator does not apply the driving force, the path length of the lumen per unit length of the guide along the longitudinal axis in the first portion of the lumen is different from the path length of the lumen per unit length of the guide along the longitudinal axis in the second portion of the lumen.

* * * * *